(12) United States Patent
Mukhopadhyay et al.

(10) Patent No.: US 7,423,015 B1
(45) Date of Patent: Sep. 9, 2008

(54) ANTIHELMINTHIC DRUGS AS A TREATMENT FOR HYPERPROLIFERATIVE DISEASES

(75) Inventors: Tapas Mukhopadhyay, Houston, TX (US); Sunil Chada, Missouri City, TX (US); Abner Mhashilkar, Houston, TX (US); Jack A. Roth, Houston, TX (US)

(73) Assignees: Board of Regents, The University of Texas System, Austin, TX (US); Introgen Therapeutics, Inc., Austin, TX (US)

( * ) Notice: Subject to any disclaimer, the term of this patent is extended or adjusted under 35 U.S.C. 154(b) by 944 days.

(21) Appl. No.: 10/043,877

(22) Filed: Jan. 9, 2002

Related U.S. Application Data

(60) Provisional application No. 60/261,346, filed on Jan. 11, 2001.

(51) Int. Cl.
*A01K 43/78* (2006.01)

(52) U.S. Cl. ................. 514/12; 514/365; 514/396; 514/397; 514/388

(58) Field of Classification Search ............. 514/365, 514/388, 396, 397; 424/450
See application file for complete search history.

(56) References Cited

U.S. PATENT DOCUMENTS

| | | | |
|---|---|---|---|
| 5,767,138 A | 6/1998 | Camden | 514/365 |
| 5,880,144 A * | 3/1999 | Camden | 514/397 |
| 5,900,429 A | 5/1999 | Camden | 514/395 |
| 5,929,099 A | 7/1999 | Camden | 514/365 |
| 6,028,116 A | 2/2000 | Sperl et al. | 514/729 |
| 6,046,206 A | 4/2000 | Pamukcu et al. | 514/259 |
| 6,077,862 A | 6/2000 | Camden | 514/388 |
| 6,211,177 B1 | 4/2001 | Sperl et al. | 514/241 |
| 6,262,059 B1 | 7/2001 | Pamukcu et al. | 514/260 |
| 6,262,093 B1 * | 7/2001 | Camden | 514/365 |
| 6,348,032 B1 | 2/2002 | Sperl et al. | 574/338 |
| 6,369,092 B1 | 4/2002 | Pamukcu et al. | 514/394 |
| 6,380,232 B1 | 4/2002 | Quada, Jr. et al. | 514/388 |
| 6,407,131 B1 | 6/2002 | Quada, Jr. et al. | 514/395 |
| 6,420,411 B1 | 7/2002 | Camden et al. | 514/395 |

FOREIGN PATENT DOCUMENTS

| | | |
|---|---|---|
| CA | 2 342 470 | 9/2002 |
| WO | WO 98/32440 | 7/1998 |
| WO | WO 98/51304 | 11/1998 |
| WO | WO00/41669 | * 7/2000 |
| WO | WO 00/41669 | 7/2000 |
| WO | WO 02/076454 A1 | 10/2002 |

OTHER PUBLICATIONS

Perdoma et al., J. Cancer Res. Clin. Oncol. 1998, 124, 10-18.*
Perdoma et al. (J. Cancer Res. Clin. Oncol. 1998, 124, 10-18).*
Delatour et al. (Therapie 1976; 31 (4); 505-515).*
Freshney (Culture of Animal Cells, A Manual of Basic Technique, Alan R. Liss, Inc., 1983, New York, p. 4).*
Dermer (Bio/Technology, 1994, 12:320).*
Delatour et al. (IDS, Therapie 1976; 31 (4); 505-515).*
Nasr et al. (Journal of Pharmaceutical Sciences 1985; 74: 831-836).*
Lucci et al. (Cancer; 86:300-311, published online on Nov. 2000).*
Su et al. (PNAS 1998; 95: 14400-14405).*
Perdoma et al. ( J. Cancer Res. Clin. Oncol. 1998, 124, 10-18).*
Albonico et al., "Control strategies for human intestinal nematode infections," *Adv. Parasitol.*, 42:277-341, 1999.
Braithwaite et al., "Clinical pharmacokinetics of high dose mebendazole in patients treated for cystic hydatid disease," *Eur. J. Clin Pharmacol.*, 22:161-169, 1982.
Braithwaite et al., "Cyst and host tissue concentrations of mebendazole in patients undergoing surgery for hydatid disease," *The Medical J. of Australia*, 2:383-384, 1983.
Bryceson et al., "Bioavailability and tolerability of mebendazole in patients with inoperable hydatid disease," *Trans. of the Royal Soc. Of Tropical Med. And Hygiene*, 76:563-564, 1982.
Burgat-Sacaze et al., "Bound residues of veterinary drugs: bioavailability and toxicological implications," *Ann. Rech. Vet.*, 13:277-289, 1981.
Chiba et al., "Improvement of dissolution and bioavailability for mebendazole, an agent for human echinococcosis, by preparing solid dispersion with polyethylene glycol," *Chem. Pharm Bull.*, 39(8):2158-2160, 1991.
Dawson and Watson, "The effect of dose form on the bioavailability of mebendazole in man," *Br. J. Clin Pharmac.*, 19:87-90, 1985.
Dawson et al., "The pharmacokinetics and bioavailability of mebendazole in man: a pilot study using [$^3$H]-mebendazole," *Br. J. Clin Pharmac.*, 14:453-455, 1982.
Delatour and Richard, "Embryogenic and antimitotic properties of benzimidazole series," *Therapie*, 31:505-515, 1976, with English translation.
Delatour et al., "Embryotoxic and antimitotic properties of parbendazole, mebendazole and cambendazole," *C R Acad Sci Hebd Seances Acad Sci D*, 282(5):517-518, 1976, with English translation.
Description of Vermox® (mebendazole), pp. 1442 From *Physicians' Desk Reference*, Janssen Pharmaceutica, c1998.
Edwards and Breckenridge, "Clinical pharmacokinetics of anthelmintic drugs," *Clin. Pharmacokinet.*, 15:67-93, 1988.
Elhajouji et al., "Indication for thresholds of chromosome non-disjunction versus chromosome lagging induced by spindle inhibitors in vitro in human lymphocytes," *Mutagenesis*, 12:133-140, 1997.

(Continued)

*Primary Examiner*—Brandon J Fetterolf
(74) *Attorney, Agent, or Firm*—Fulbright & Jaworski L.L.P.

(57) ABSTRACT

The present invention is directed to the use of benzimidazole derivatives for the treatment of tumors and in combination with tumor suppressor gene therapy. In a particular embodiment, treatment of p53-positive tumors with benzimidazole derivatives induces p53 expression and increases its half-life, resulting in apoptotic death of the tumor cells. Similarly, in conjunction with p53 gene therapy, benzimidazole derivatives induce p53 expression and accumulation in tumor cells regardless of their p53 status. The combination treatment subsequently elicits apoptosis of the tumor cells.

57 Claims, 11 Drawing Sheets

OTHER PUBLICATIONS

Farghali and Masek, "Immunopharmacologic agents in the amelioration of hepatic injuries," *International J. of Immunopharmacology*, 20:125-139, 1998.

Galtier et al., "Fasciola hepatica: mebendazole and thiabendazole pharmacokinetics in sheep," *Exp. Parasitology*, 79:166-176, 1994.

Kromer, "Similarities and differences in the properties of substituted benzimidazoles: a comparison between pantoprazole and related compounds," *Digestion*, 56:443-454, 1995.

Lubega and Prichard, "Interaction of benzimidazole anthelmintics with *Haemonchus contortus* tubulin: binding affinity and anthelmintic efficacy," *Exp. Parasitol.*, 73:203-213, 1991.

Lubega and Prichard, "Specific interaction of benzimidazole anthelmintics with tubulin from developing stages of thiabendazole-susceptible and resistant *Haemonchus contortus*," *Biochem. Pharacol.*, 41:93-101, 1991.

Michiels et al., "The pharmacokinetics of mebendazole and flubendazole in animals and man," *Arch. Int. Pharmacodyn.*, 256:180-191, 1982.

Upton, "Pharmacokinetic interactions between theophylline and other medication (Part I)," *Clin. Pharmacokinet.*, 20:66-80, 1991.

Van Hummelen et al., "Clastogenic and aneugenic effects of three benzimidazole derivatives in the in vitro micronucleus test using human lymphocytes," *Mutagenesis*, 10:23-29, 1995.

Bossche et al., *Chemotherapy of Gastrointestinal Helminths.*, Arundel et al., (eds.), Springer-Verlag, 1985, In: Handbook of Experimental Pharmacology, vol. 77, Born et al., (eds.).

Davidse, "Benzimidazole fungicides: mechanism of action and biological impact," *Ann. Rev. Phytopathol.*, 24:43-65, 1986.

Friedman and Platzer, "Interaction of anthelmintic benzimidazoles and benzimidazole derivatives with bovine brain tubulin," *Biochim. Biophys. Acta*, 544:605-614, 1978.

Friedman and Platzer, "Interaction of anthelmintic benzimidazoles with ascaris suum embronic tubulin," *Biochim. Biophys. Acta*, 630:271-278, 1980.

Gottschall et al., "The metabolism of benzimidazole anthelmintics," *Parasitol. Today*, 6:115-124, 1990.

Kohler and Bachmann, "Intestinal tubulin as possible target for the chemotherapeutic action of mebendazole in parasitic nematodes," *Mol. Biochem. Parasitol.*, 4:325-336, 1981.

Lacey and Prichard, "Interactions of benzimidazoles (BZ) with tubulin from BZ-sensitive and BZ-resistant isolates of *Haemonchus contortus*," *Mol Biochem Parasitol*, 19:171-181, 1986.

Lacey and Watson, "Structure-activity relationships of benzimidazole carbamates as inhibitors of mammalian tubulin, in vitro," *Biochem. Pharmacol.*, 34(7):1073-1077, 1985.

Lacey and Watson, "Activity of benzimidazole carbamates against L1210 mouse leukaemia cells: correlation with in vitro tubulin polymerization assay," *Biochem. Pharmacol.*, 34(19):3603-3605, 1985.

Lacey, "The role of the cytoskeletal protein, tubulin, in the mode of action and mechanism of drug resistance to benzimidazoles," *Int. J. Parasitol.*, 18:885-936, 1988.

Lanusse et al., "Methimazole-mediated modulation of netobimin biotransformation in sheep: a pharmacokinetic assessment," *J Vet Pharmacol Ther*, 15(3):267-274, 1992.

Lanusse et al., "Comparative sulphoxidation of albendazole by sheep and cattle liver microsomes and the inhibitory effect of methimazole," *Xenobiotica*, 23(3):285-295, 1993.

Lubega, and Prichard, "Specific interaction of benzimidazole anthelmintics with tubulin: high-affinity binding and benzimidazole resistance in *Haemonchus contortus*," *Mol. Biochem. Parasitol.*, 38:221-232, 1990.

Nare et al., "Benzimidazoles, potent anti-mitotic drugs: substrates for the P-glycoprotein transporter in multidrug-resistant cells," *Biochem. Pharmacol.*, 48(12):2215-2222, 1994.

Nare, et al., "p-azidosalicyl-5-amino-6-phenoxybenzimidazole photolabels the N-terminal 63-103 amino acids of *Haemonchus contortus* β-Tubulin 1," *J Biol Chem*, 271(15):8575-8581, 1996.

Pilch et al. "Characterizing the DNA binding modes of a topoisomerase 1-poisoning terbenzimidazole: evidence for both intercalative and minor groove binding properties," *Drug Des Discov*, 13:115-133, 1996.

Russell et al., "Binding of [$^3$H]Benzimidazole carbamates to mammalian brain tubulin and the mechanism of selective toxicity of the benzimidazole anthelmintics," *Biochem. Pharmacol.*, 43(5):1095-1100, 1992.

Stearns et al., "Liarozole and 13-cis-retinoic acid anti-prostatic tumor activity," *Cancer Res*, 53:3073-3077, 1993.

Delatour et al., "Embrytoxic and antimitotic properties of benzimidazole compounds," *Therapie*, 31:505-515, 176.

Lacey et al., "Activity of benzimidazole against L1210 mouse leukaemia cells: Correlation with in vitro tubulin polymerization assay," *Biochem. Pharmacol.*, 34:3603-3605, 1985.

Penman et al., "Omeprazole inhibits colorectal carcinogenesis induced by azoxymethane in rats," *Gut*, 34:1559-1565, 1993.

Ram et al., "Synthesis and biological activity of certain alkyl 5-(Alkoxycarbonyl)-1*H*-2-carbamates and related derivatives: A new class of potential antineoplastic and antifilarial agents," *Journal of Medicinal Chemistry*, 35:539-547, 1992.

Tobi et al., "Omeprazole inhibits growth of cancer cell line of colonic origin," *Dig. Dis. Sci.*, 40: 1526-1530, 1995.

Atassi and Tagnon, "R17934-NSC 238159: a new antitumor drug—I. Effect on experimental tumors and factors influencing effectiveness," *Europ. J. Cancer*, 11:599-607, 1975.

Delatour et al., "Embrytoxic and antimitotic properties of parbendazole, mebendazole and cambendazole," *C R Acad Sci Hebd Seances Acad Sci D*, 282(5):517-518, 1976, article in French.

Lapras and Delatour, "Propertietes antimitotiques de certains anthelminthiques embryotoxiques et tertogenes derives du benzimidazole," *Proceedings of the European Society of Toxicology*, 18:294-296, 1977, article in French.

Styles, "Cytotoxic effects of various pesticides in vivo and in vitro," *Mutation Research*, 21:50-51, 1973.

\* cited by examiner

A
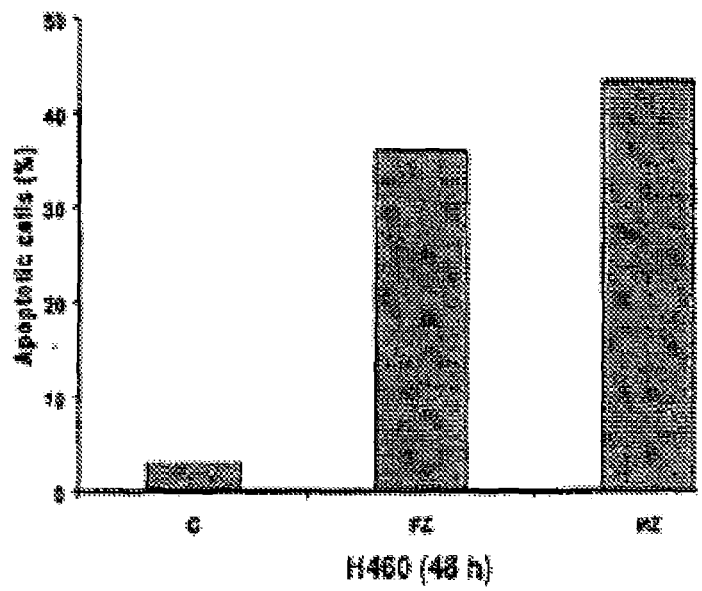
B
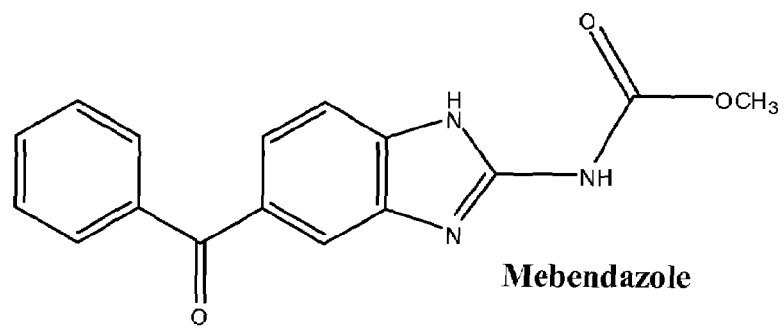
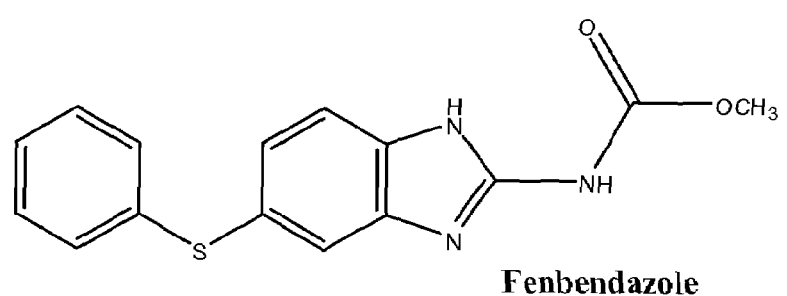
FIG. 1A-1B

ANTIHELMINTHIC DRUGS AS A TREATMENT FOR HYPERPROLIFERATIVE DISEASES

The present application claims priority to co-pending U.S. Provisional Patent Application Ser. No. 60/261,346 filed on Jan. 11, 2001. The entire text of the above-referenced disclosure is specifically incorporated herein by reference without disclaimer.

BACKGROUND OF THE INVENTION

A. Field of the Invention

The present invention relates generally to the field of cancer therapy. More particularly, it concerns the use of benzimidazoles to elicit cell death in tumor cells and to inhibit angiogenesis. In addition, benzimidazoles may be used as treatments for other hyperproliferative diseases, including rheumatoid arthritis, inflammatory bowel disease, restenosis etc.

B. Description of Related Art

1. Cancer and p53

Normal tissue homeostasis is achieved by an intricate balance between the rate of cell proliferation and the rate of cell death. Disruption of this balance is thought to be a major deleterious event in the development of cancer. The inhibition of apoptosis (programmed cell death) has been linked to this disruptive event. The effects of such defects are catastrophic, causing over half a million deaths per annum in the United States alone.

It is well recognized that the expression of a tumor suppressor gene frequently inhibits cell growth and often induces apoptosis in a tumor cell. The p53 gene is a well known example of such a tumor suppressor gene (Monthenarh, 1992). There is now considerable evidence linking mutations of p53 and other tumor suppressor genes in the oncogenesis of many human cancers. There are numerous reports demonstrating that the growth of, for example, colon, glioblastoma, breast cancer, osteosarcoma and lung tumor cells can be suppressed by the expression of wild-type tumor suppressor genes.

For example, the introduction of wild-type p53 to a wide variety of p53-mutated tumor cells is sufficient to suppress of the malignant phenotype. These observations demonstrate that a high level of expression of wild-type p53 is a desirable course for the treatment of oncogenic malignancy.

As the half-life of p53 is very short, ranging between 15 and 20 minutes, it has proven difficult to increase the intracellular levels of p53 using conventional transfection strategies. The microcellular environment of these cells is such that overexpression of wild-type p53 protein, when achieved, is counteracted by rapid degradation. Hence, delivery of wild-type p53 into cancer cells using conventional viral vectors as a way of reducing tumor growth is at best inefficient.

The limitations in increasing the expression of exogenous p53 using conventional transfection strategies is exemplary of the constraints on sustained expression of other exogenous tumor suppressor genes. Therefore, there is a clear need for approaches to sustain induction or increase in tumor suppressor gene expression in cancer cells to mediate apoptosis in such cancer cells.

2. Angiogenesis

Angiogenesis, the development of new capillaries from preexisting blood vessels, plays a critical role in a variety of physiological processes and pathological conditions, including embryonic development, wound healing, tumor growth, metastasis, and various inflammatory disorders (Folkman, 1995a). It is now well documented that angiogenesis is required for metastasis and growth of solid tumors beyond a few cubic millimeters in size (Folkman, 1972; 1995b). Indeed, many research teams are exploring the therapeutic potential of such angiogenesis inhibitors as angiostatin, an ~38-40-kDa fragment of plasminogen, endostatin (an ~18-kDa fragment of collagen XVIII), transforming growth factor, thrombospondin-1, fumagillin, 2-methoxyestradiol, and thalidomide. This continues to be a promising area of cancer research.

SUMMARY OF THE INVENTION

The present invention provides methods for inducing growth arrest or killing of hyperproloferative or tumor cells comprising the administration of an anti-helminthic agent. The present invention provides methods for inducing apoptosis in a cell expressing a functional tumor suppressor, or in a cell not expressing a functional tumor suppressor gene but further comprising the administration of exogenous tumor suppressor gene. The present invention further provides improved methods for the treatment of cancers comprising (a) administration of a tumor suppressor gene in conjunction with an agent that increases the level of a tumor suppressor gene in cells, (b) administration of the agent alone to a tumor suppressor expressing cell, or (c) administration of the agent in combination with chemtherapy or radiotherapy.

In accordance with the present invention, there is provided a method for inducing apoptosis in a cell having a functional tumor suppressor gene therein, comprising the step of contacting the cell with an amount of benzimidazole or a similar agent sufficient to increase the level and/or activity of tumor suppressor gene in the cell. The tumor suppressor may be an endogenous or exogenous protein. The benzimidazole may be a derivative, for example, fenbendazole or mebendazole. The cell may be a tumor cell, for example, a lung tumor cell such as a non-small cell lung carcinoma cell. In some embodiments, the tumor cell may be a multidrug resistant cell.

In another embodiment, there is provided a method for inducing apoptosis in a cell comprising the steps of administering to the cell a vector comprising a polynucleotide sequence encoding a tumor suppressor gene operable linked to a transcription control region, and contacting the cell with an amount of benzimidazole sufficient to induce apoptosis in the cell. The tumor suppressor gene may be p53, p16, p21, Rb, p15, BRCA1, BRCA2, zac1, p73, ATM, HIC-1, DPC-4, FHIT, NF2, APC, DCC, PTEN, ING1, NOEY1, NOEY2, PML, OVCA1, MADR2, WT1, 53BP2, IRF-1, MDA-7 or C-CAM. The benzimidazole may be a derivative, for example, fenbendazole or mebendazole. The cell may be a tumor cell, for example, a lung tumor cell such as a non-small cell lung carcinoma cell. In some embodiments, the tumor cell may be a multidrug resistant cell. The vector may be a viral (i.e., adenovirus, retrovirus, adeno-associated virus, polyoma virus, vaccinia virus, lentivirus) or a nonviral (i.e., liposomes, receptor-mediated transfection).

In yet another embodiment, there is provided a method for treating cancer in a patient comprising the steps of (a) determining the tumor suppressor gene status of a tumor cell in the patient; and (b) contacting the tumor cell with an amount of benzimidazole sufficient to induce apoptosis in the cell. Where the tumor suppressor gene status of the tumor cell is that it contains a functional tumor suppressor gene, further provision of tumor suppressor gene may be unnecessary. Where the tumor suppressor gene status of the tumor is that it lacks a functional tumor suppressor protein, the method further comprises the transfer of a wild-type tumor suppressor gene into the tumor cell. The transfer of a wild-type tumor suppressor gene may be administered using a viral or non-viral vector. Administration of the benzimidazole may be systemic, intratumoral, in the area local to the tumor, or in the area regional to the tumor.

In a particular embodiment, the transfer of a p53 gene comprises contacting the tumor cell with an adenovirus containing the wild-type p53 gene. The adenovirus may be replication defective, and in particular, may be lacking at least a portion of the E1 region. The tumor cell may be a non-small cell lung carcinoma cell. The tumor cells may have wild-type, mutant or no endogenous p53. In some embodiments, the tumor cell may be a multidrug resistant cell. In yet another embodiment, the multidrug resistant cells may have wild-type, mutant or no endogenous p53.

In another embodiment, there is provided a method for treating a patient with a hyperproliferative disorder comprising administering to said subject an amount of a benzimidazole effect to kill or inhibit the growth of hyperproliferative cells within said patient. The hyperproliferative disorder may be cancer, arthritis, IBD, restenosis etc. The method may further comprise treating the patient with an anti-cancer therapy selected from the group consisting of a chemotherapy, a radiotherapy, an immunotherapy, or a gene therapy.

In yet another embodiment, there is provided a method for inhibiting angiogenesis in a subject comprising administering to said subject an amount of a benzimidazole effective to inhibit angiogenesis in said subject. The vascular development may be caused by or ancillary to a hyperproliferative disorder, for example, a cancer. The method may further comprise treating the patient with an anti-cancer therapy selected from the group consisting of a chemotherapy, a radiotherapy, an immunotherapy, or a gene therapy.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1B: Induction of Apoptosis. FIG. 1A—Induction of apoptosis was assessed by TdT FACS analysis in the human lung cancer cell line, H460. Cells were harvested after 24 hr exposure to FZ and MZ (0.05 μg/ml) and the apoptotic cells quantitated after TdT staining as described in the Examples. FIG. 1B—Chemical structure of MZ and FZ.

FIG. 4A—Cell growth was measured in untreated controls, cells treated with 0.05 ng/ml FZ and cells treated with the combination of Ad5p53 (1 MOI) and FZ. FIG. 4B—H322 cells also were treated with empty adenoviral vector, dl312, in addition to Adp53 to show dl312 had no effect alone or in combination with FZ. FIG. 4C—A549 lung cancer cells were examined for apoptotic cell death 48 h after FZ and Ad5p53 treatment alone or in combination. Percent apoptotic cells were measured by TdT-FACS analysis.

FIG. 5A. Dose-dependent inhibition of cell proliferation after mebendazole treatment. Human NSCLC tumor cell lines (H460 and A549) and normal endothelial (HUVEC) and normal fibroblast (WI-38) cell lines were used for this assay. FIG. 5B. Time course of the growth of human xenograft. Athymic nu/nu mice were injected with H460, a human non-small cell lung cancer cell line ($2 \times 10^4$ cells/mouse) and about 12 days later mice with established tumors (3-4 mm) were fed with 100 μl (1 mg) MZ suspension in PBS using an intubation tube every second day until they were sacrificed. FIG. 5C. H460 cells were injected into animals ($2 \times 10^4$ cells/mouse), animals with established tumors (3-4 mm) were fed with different concentrations of MZ every alternate day while control animals received PBS only (C). T0.2, T0.4 and T0.8 correspond to 0.2, 0.4 and 0.8 mg of MZ treatment groups. FIG. 5D. Graphical representation of tumor weight in mg ±s.d. of both control and mebendazole-treated tumors on day 28.

DESCRIPTION OF ILLUSTRATIVE EMBODIMENTS

Figure 2:
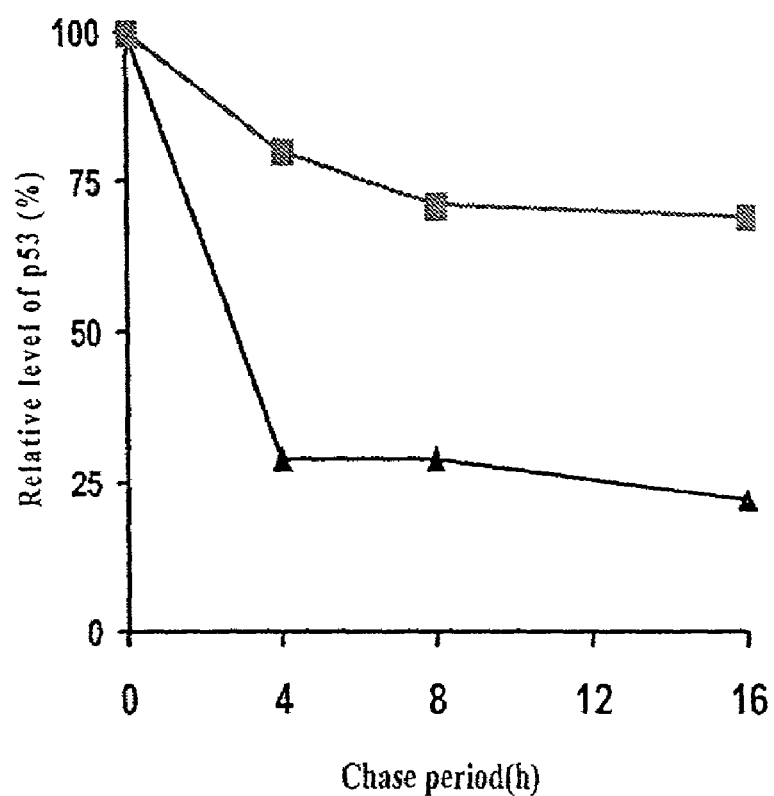
FIG. 2: Effect of FZ and MZ on the Stability of the p53 Protein. p53 protein stability in cells. Data from the pulse-chase experiments were quantitated with a PhosphoImager using ImageQuant™ software. Circles and triangles represent data from FZ-treated and control samples, respectively.

Cancer accounts the death of over half a million people a year in the United States alone. The causes for cancer are multifactorial, however, it is known that aberrations in controlled cell death result in uncontrolled cell proliferation and hence contribute to many cancers. One common cause of cancer is the loss of tumor suppressor function.

Many attempts have been made to augment the wild-type tumor suppressor gene expression in tumor cells through gene therapy techniques. These attempts, although potentially valuable, have generally been limited for a number of reasons including low levels and a very short half life.

The present invention provides a means of increasing the level and/or activity of a tumor suppressor gene in tumor cells, thereby, allowing for an increased incidence of apoptosis. The inventors have discovered that the benzimidazoles (BZs), fenbendazole (FZ) and mebendazole (MZ) can increase the expression of tumor suppressor genes and greatly augment the sensitivity of tumor cells to apoptosis induction. Furthermore, by combining BZ with pro-apoptotic agents, such as chemotherapeutics, radiation or gene therapy, enhanced levels of cell death and apoptosis are achieved. This finding can be employed in a number of ways. First, cancers that express normal tumor suppressor genes can be treated with BZs as disclosed herein, thereby increasing the levels of tumor suppressor gene and helping to induce apoptosis. Second, the compositions of the present invention can be used to augment conventional gene therapy, where wild-type tumor suppressor gene is introduced into tumor cells. The addition of the BZ to the regimen increases the level and/or activity of the tumor suppressor gene, inducing or enhancing cell death. A third way in which the present invention is employed is in combination therapy, where gene therapy is used in combination with conventional chemotherapy, and the BZ is used to increase wild-type tumor suppressor gene expression and/or function thereby inducing programmed cell death. Fourthly, benzimidazoles constitute a novel class of chemotherapeutic drugs for the treatment of hyperproliferative disorders. These drugs can be combined with conventional chemotherapeutics such as cisplatin, carboplatin, adriamycin, taxol etc. and enhance tumor cell killing.

In a separate embodiment of the present invention, the inventors will exploit another valuable action of BZ—the inhibition of angiogenesis. Since angiogenesis is a key aspect of tumor progress, BZ's ability to inhibit this process provides yet another avenue through which this class of compounds can be used, either alone or in combination, to combat cancer.

In some embodiments of the present invention, the inventors have developed tumor cells that are multi-drug resistant to microtubule-active drugs such as taxol and vinorelbine. "Multi-drug resistance (DR)" is a generic term for the variety of strategies tumor cells use to evade the cytotoxic effects of anticancer drugs. MDR is characterized by a decreased sensitivity of tumor cells not only to the chemotherapeutic drug but also to a broad spectrum of drugs with neither obvious structural homology nor common targets. MDR may result from structural or functional changes at the plasma membrane or within the cytoplasm, cellular compartments, or nucleus of the cell. Resistance to more drugs than selected for is also predicted by the hypothesis that drug resistance is achieved by chromosome reassortments that simultaneously vary thousands of genes. Several such cross-resistances have also been confirmed for the cells studied. The inventors have discovered that the benzimidazoles (BZs) such as mebendazole (MZ) can be used to effectively kill multi-drug resistant cells.

A. BENZIMIDAZOLES

Benzimidazoles (BZs) are broad-spectrum antihelmintics that display excellent activity against parasitic nematodes and, to a lesser extent, against cestodes and trematodes (Bossche et al., 1985). BZs have also been shown to be very effective antiprotozoal agents and to have antifungal activity (Davidse, 1986). It is currently believed that BZs exert their cytotoxic effects by binding to the microtubule system and disrupting its functions (Lacey, 1988; Friedman and Platzer, 1980). The suggestion that tubulin is a target for BZs has been supported by the results of drug-binding studies using enriched extracts of helminth and mammalian tubulin (Lacey, 1988). Moreover, competitive drug-binding studies using mammalian tubulin have shown that BZs compete for colchicine binding and inhibit growth of L1210 murine leukemia cells in vitro (Friedman and Platzer, 1978; Lacey and Watson, 1989). However, BZs are selectively toxic to nematodes when administered as antihelmintics but are not toxic to the host (Bossche et al., 1985). In contrast, BZs suppress the in vitro polymerization of mammalian tubulin (Davidse, 1986). Differences in both the affinity between the host and parasite macromolecules for BZ (Russell et al., 1992; Kohler and Bachmann, 1981) and the pharmacokinetics of BZs between the host and the parasite have been suggested as responsible for the selective toxicity of BZs (Gottschall et al., 1990) but the actual molecular basis of this selective toxicity remains unclear.

Benzimidazoles have the formula:

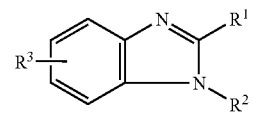

wherein R is selected from the group consisting of H, carboxyl (—$CO_2H$), hydroxyl, amino or esters (—$CO_2R'$) wherein R' is selected from the group consisting of alkoxy, haloalkyl, alkenyl, and cycloalkyl wherein the alkyl groups have 1-8 carbons or $CH_3CH_2(OCH_2CH_2)_n$— or $CH_3CH_2CH_2(OCH_2CH_2CH_2)_n$— or $(CH_3)_2CH(OCH(CH_3)—CH_2)_n$— wherein n is from 1-3 and the pharmaceutically acceptable organic or inorganic addition salts thereof; wherein $R^3$ is selected from the group consisting of H, carboxyl (—$CO_2H$), hydroxyl, amino, chloro, difluormethoxy, benzoyl, phenyl-thio, pyridinyl, propyl-thio, diphenyl, methoxy(methoxy-dimethyl,pyridinyl)methyl-(sulfonyl), fluorophenylmethyl-2-chloro, propenyl, chloroprophyl or esters (—$CO_2R^4$) wherein $R^4$ is selected from the group consisting of alkoxy, haloalkyl, alkenyl, and cycloalkyl, wherein the alkyl groups have from 1-8 carbons, or $CH_3CH_2(OCH_2CH_2)_n$—, or $CH_3CH_2CH_2(OCH_2CH_2CH_2)_n$—, or $(CH_3)_2CH(OCH(CH_3)CH_2)_n$—, wherein n is from 1-3, wherein $R^1$ is OH, Cl, SH, carbamate or piperidin-4-yl, and $R^2$ is hydrogen, α-methylvinyl, 3-chloropropyl or piperidin-4-yl, or the pharmaceutically effective organic or inorganic salts thereof, or mixtures thereof. For $R^4$, the preferred alkyl groups are straight chain, the preferred the halogen is substituted on the terminal carbon, the preferred halogen is chlorine, the preferred cycloalkyl groups are those having 3-6 carbon atoms, and the cycloalkyl groups also include those which are substituted on an alkyl chain, 2-cyclopropylethyl, cyclopropylmethyl, 2-cyclopropylpropyl or 2-cyclopropylpropyl or cyclohexylmethyl.

BZs have some anti-tumor growth properties in vitro (WO 98/513304; WO 98/32440). The efficacy of BZs in vivo as an anti-tumor treatment has been limited to tumors already in regression following chemotherapeutic treatment.

Alternative benzimidazoles are: Fenbendazole, albendazole, albendazole sulfone, oxibendazole, rycobendazole, thiabendazole, oxfendazole, flubendazole and carbendazim.

Alternative anti-helminthic drugs are the imidazoles: niridazole and levimasole, the piperazines: piperazine and diethylcarbamazine, the isothiocyanates: amoscanate and CGP 6140. In addition, suramin, ivermectin, hycanthone, metrifonate, oxamniquine and praziquantel are anti-helminthic drugs

B. TUMOR SUPPRESSOR GENES p53 currently is recognized as a tumor suppressor gene. High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers. It is mutated in over 50% of human NSCLC (Hollestein et al., 1991) and in a wide spectrum of other tumors.

The p53 gene encodes a 393-amino-acid phophoprotein that can form complexes with host proteins such as large-T antigen and E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are know to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through $G_1$. The activity of CDK4 is controlled by an activating subunit, D-type cylcin, and by an inhibitory subunit $p16^{INK4}$. The $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in the hyperphosphorylation of the Rb protein. p16 is also known to regulate the function of CDK6.

$p16^{INK4}$ belongs to a newly described class of CDK-inhibitory proteins that also include $p15^{INKB}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al., 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type $p16^{INK4}$ function by transfection with a plasmid expression vector reduced colony formation by some human cancer cell lines (Okamoto, 1994; Arap, 1995). Delivery of p16 with adenovirus vectors inhibits proliferation of some human cancer cell lines and reduces growth of human tumor xenografts.

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, (Cheung et al., 1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, (Giancotti and Ruoslahti 1990) demonstrated that increasing expression of $\alpha 5\beta 1$ integrin by gene transfer can reduce tumorigenicity of Chinese hamster ovary cells in vivo. C-CAM now has been shown to suppress tumor growth in vitro and in vivo.

Melanoma differentiation-associated (MDA) genes correlate with or directly influence human melanoma cell growth and differentiation (Su et al., 1998). Recent studies have demonstrated that the anti-tumorigenic activity of the MDA family members is not limited to melanomas. The expression of MDA-7 inhibited the growth of glioblastoma, osteosarcoma, colorectal cancer, breast cancer, cervical cancer and nasopharyngeal cancer in vitro (Jiang et al., 1996). MDA-7 expression suppressed the growth in human breast cancer cells in vitro by inducing apoptosis and in vivo in a xenograft model (Su et al., 1998).

Other tumor suppressors that may be employed according to the present invention include BRCA1, BRCA2, zac1, p73, MMAC-1, ATM, HIC-1, DPC-4, FHIT, NF2, APC, DCC, PTEN, ING1, NOEY1, NOEY2, PML, OVCA1, MADR2, WT1, 53BP2, and IRF-1.

C. TREATMENT OF CANCERS USING BENZIMIDAZOLES

A patient presenting with cancer may be treated with the benzimidazole alone. Of particular interest are patients that have wild-type tumor suppressor (e.g., p53) function. The tumor suppressor status of the tumor cells can be determined using any conventional methods, examples of which are described below. Patients may, but need not, have received previous chemo-, radio-, or gene therapies. Optimally, patients will have adequate bone marrow function (defined as peripheral absolute granulocyte count of >2000/mm$^3$ and platelet count of 100,000/mm$^3$), adequate liver function (bilirubin $\leq$1.5 mg/dl) and adequate renal function (creatinine <1.5 mg/dl).

The patient will be treated with a pharmaceutically acceptable form of BZ or a functional analog thereof. This administration could be in the form of, for example, an intratumoral injection, or indeed, any other method of application that is routinely used and well known to one of skill in the art, e.g., oral, systemic, local, regional. A biopsy of the lesions to be injected may be performed and the tissue stored for immunohistochemistry analyses.

The dose of BZ typically will be reconstituted into a pharmaceutically acceptable form immediately prior to administration. The starting dose will be 0.1 to 1 mg BZ/kg body weight. Of course this may vary depending on the size of the tumor, the rate at which the tumor is growing, etc. The treatment will be administered daily over a four-week period. During this time, the tumor will be monitored for absence of tumor progression, response or toxicity and the doses adjusted accordingly. Alternative dosing regimens will use administration of BZ on alternate days, or twice or one per week. Cumulative doses can be up to 2000-3000 mg, given either in bolus administrations over 2-3 days or in divided doses over a longer timeperiod, ranging from 1 week to 2-4, 4-8, 8-12, 12-16 weeks.

1. Determination of Tumor Suppressor Status of Cells

A wide variety of detection methods can be employed in the present invention to detect the tumor suppressor status of a cell. There are numerous antibodies to the tumor suppressor protein, hence, any assay that utilizes antibodies for detection, for example, ELISAs, Western blotting, and other immunassay techniques, may be used to identify p53 protein. Alternatively, assays that employ nucleotide probes may be used to identify the presence/absence of an intact tumor suppressor gene, for example, Southern blotting, Northern blotting or PCR techniques.

All the above techniques are well known to one of skill in the art and could be utilized in the present invention without undue experimentation.

i. Immunoassay and Immunohistological Assay

Immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the anti-tumor suppressor specific antibodies are immobilized onto a selected surface exhibiting protein affinity, such as a well in a polystyrene microtiter plate. Then, a test composition containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

Variations of ELISA techniques are known to those of skill in the art. In one such variation, the samples containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable level.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of mild powder. The coating allows for blocking of nonspecific adsorption sites on the immobilizing surface and thus reduces the background caused by nonspecific binding of antisera onto the surface.

In ELISAs, it is probably more customary to use secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of the nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for two hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic-acid (ABTS) and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for the p53 status of the cell also can determine normal/abnormal tissue distribution for diagnostic purposes. Methods for in vitro and in situ analysis are well known and involve assessing binding of antigen-specific antibodies to tissues, cells or cell extracts. These are conventional techniques well within the grasp of those skilled in the art. For example, the antibodies to the tumor suppressor may be used in conjunction with both fresh-frozen and formalin-fixed, paraffin-embedded tissue blocks prepared for the study by immunohistochemistry (IHC). Each tissues block may consist of 50 mg of residual "pulverized" tumor. The method of preparing tissue blocks from these particulate specimens has been successfully used in previous IHC studies of various prognostic factors, e.g., in breast cancer, and is well known to those of skill in the art (Abbondanzo et al., 1990; Allred et al., 1990; Brown et al., 1990).

Briefly, frozen sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissues cylinder on a cryostat microtome chuck; and cutting 25-50 serial sections containing an average of about 500 remarkably intact tumor cells.

Permanent sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

ii. Southern and Northern Blotting Techniques

Southern and Northern blotting are commonly used techniques in molecular biology and well within the grasp of one skilled in the art.

For Southern blots, the DNA from test cells is recovered by gentle cell rupture in the presence of a cation chelator such as EDTA. The proteins and other cell milieu are removed by admixing with saturated phenol or phenol/chloroform and centrifugation of the emulsion. The DNA is in the upper aqueous phase, it is deproteinised and mixed with ethanol. This solution allows the DNA to precipitate and the DNA can then be recovered using centrifugation.

Electorphoresis in agarose or polyacrylamide gels is the most usual way to separate DNA molecules. Southern blotting will confirm the identity of the tumor suppressor encoding DNA. This is achieved by transferring the DNA from the intact gel onto nitrocellulose paper. The nitrocellulose paper is then washed in buffer that has for example, a radiolabelled cDNA containing a sequence complementary to wild-type tumor suppressor DNA. The probe binds specifically to the DNA that encodes at least a portion of tumor suppressor and can be detected using autoradiography by contacting the probed nitrocellulose paper with photographic film.

Tumor suppressor encoding mRNA can be detected in a similar manner by a process known as Northern blotting. For more detailed description of buffers, gel preparation, electrophoresis conditions, etc., the skilled artisan is referred to (Sambrook et al., 1989).

iii. Polymerase Chain Reaction (PCR)

PCR is a powerful tool in modern analytical biology. Short oligonucleotide sequences usually 15-35 bp in length are designed, homologous to flanking regions either side of the sequences to be amplified. Primers are added in excess to the source DNA, in the presence of buffer, enzyme, and free nucleotides. The source DNA is denatured at 95° C. and then cooled to 40-50° C. to allow the primers to anneal. The temperature is adjusted to the optimal temperature for the polymerase for an extension phase. This cycle is repeated 25-40 times.

In particular the present invention uses PCR to detect the tumor suppressor gene status of cells. For example, mutations in the tumor suppressor gene are first detected with Single Strand Confirmation Polymorphism (SSCP) which is based on the electorphoretic determination of conformational changes in single stranded DNA molecules induced by point mutations or other forms of slight nucleotide changes. To identify where the mutation is located within the p53 gene, each exon is separately amplified by PCR using primers specific for the particular exon. After amplification, the PCR product is denatured and separated out on a polyacrylamide gel to detect a shift in mobility due to a conformational change which resulted because of a point mutation or other small nucleotide change in the gene. Mutations result in a change in the physical conformation of the DNA as well as change in the electrical charge of the molecule. Thus, during electrophoresis when an electrical charge is applied to the molecule, DNA that is slightly different in shape and charge as compared to wild type will move at a different rate and thus occupy a different position in the gel.

After determination of which DNA fragment contains the mutation, the specific nucleotide changes are detected by DNA sequencing of the amplified PCR product. Sequencing of linear DNA breaks down the DNA molecule into its individual nucleotides in the order with which they are assembled in the intact molecule. Separation of the individual nucleotides by electrophoresis on a sequencing gel allows detection of individual nucleotide changes compared to wild-type and is used to determine homo- or heterozygocity of a mutation, which is easily distinguished by the appearance of a single or double band in the sequencing gel.

2. Pharmaceutical Compositions and Routes of Administration

Aqueous compositions of the present invention will have an effective amount of a BZ compound that increases the expression of wild-type tumor suppressor genes, and/or inhibits angiogenesis. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets and other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains a compound or compounds that increase the levels of wild-type p53 will be within the skill of those in the art, in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitable mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in aqueous solution, for example, the solution should be suitably buffered if necessary, and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see, for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Many benzimidazoles are only sparingly soluble in aqueous solutions. It is therefore an aspect of the current invention that the BZ compound be in a formulation which allows for an increased solubilization of the benzimidazole or for a more effective dispersion.

Surfactants can be added to the aqueous solution to increase solubility and stability of a solution or dispersion. Surfactants are organic molecules which contain both hydrophilic and hydrophobic ends. The hydrophilic end, which is either polar or ionic, dissolves readily in water. The hydrophobic, or non-polar, end, however, does not dissolve in water and will move as far away from water as possible. When a small concentration of surfactant is added to water, the hydrophobic end will immediately rise to the surface or orient towards a less polar group. The addition of surfactants in a benzimidazole solution increase the solubility and/or stability of the benzimidazole-surfactant solution relative to the benzimidazole alone.

The benzimidazole may be processed to increase the stability or solubility in a solution. The formulation may be processed to a very fine size. This process is called micronizing for particles smaller than about 20 μm. Size reduction of the compound or mixture preferentially occurs through the use of a mechanical or pneumatic milling systems. Particle to particle collision, tangential fluid energy mills or pancake mills can be used (http://www.pharmaceutical-technology.com/contractors/contract/micronl).

Other methods for obtaining an aqueous composition containing a BZ compound are contemplated. An emulsion, or capsulization, such as with a soft geletin capsule may be used. An emulsion is a two part system containing two immiscible liquids. One of the liquids is uniformly dispersed in the other and consists of globules with a diameter greater than that of a colloidal suspension. An emulsion requires an emulsifying agent to prevent the separation of the two components into two phases. Emulsifying agents include natural emulsifying agents which are derived from animal or vegetable (e.g., gelatin, egg yolk, casein, or cholesterol), finely divided solids (e.g., bentonite, magnesium hydroxide, aluminum hydroxide, or magnesium trisilicate) or synthetic emulsifying agents (e.g., sodium lauryl sulfate, benzalkonium chloride or polyethylene glycol 400 monosterate). Emulsions such as oil-in-water emulsions are preferred, and can be made by any of the procedures known in the art, such as described in (Remington, 1990).

D. TREATMENT OF CANCERS WITH MUTATED TUMOR SUPPRESSOR EXPRESSION USING BENZIMIDAZOLES IN COMBINATION WITH GENE THERAPY

In a separate embodiment of the present invention, it is envisioned that BZ will be used in combination with conventional gene therapy in the treatment of those cancers that express a mutated tumor suppressor or no tumor suppressor (e.g., p53).

It is clear that delivery of wild-type tumor suppressor into tumors that express a mutated tumor suppressor gene can overcome the deleterious effects of the tumor suppressor mutation. In the present embodiment of the invention, benzimidazole is administered to the cells along with the wild-type tumor suppressor gene thereby increasing the expression of the exogenously applied wild-type tumor suppressor. The BZ can be administered concurrently with the gene therapy, before the gene therapy or after the gene therapy. Elements utilized for gene delivery are described below.

1. Expression Vectors

Throughout this application, the term "expression construct" is meant to include any type of genetic construct containing a nucleic acid coding for a tumor suppressor gene product in which part or all of the tumor suppressor nucleic acid is capable of being transcribed and subsequently translated into a protein.

In order for the construct to effect expression of a tumor suppressor transcript, the polynucleotide encoding the tumor suppressor polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 by upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased up to 50 bp apart before activity begins to decline. Depending on the promoter, it appears that individual elements can function either cooperatively or independently to activate transcription.

The particular promoter that is employed to control the expression of a tumor suppressor polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the tumor suppressor polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of tumor suppressor polynucleotides. Table 1 lists several elements/promoters which may be employed, in the context of the present invention, to regulate the expression of tumor suppressor constructs. This list is not intended to be exhaustive of all the possible elements involved in the promotion of tumor suppressor expression, but, merely, to be exemplary thereof.

Enhancers were originally detected as genetic elements that increased transcription from a promoter located at a distant position on the same molecule of the DNA. This ability to act over a large distance had little precedent in classic studies of prokaryotic transcriptional regulation. Subsequent work showed that regions of DNA with enhancer activity are organized more like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct the initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base (EPDB)) could also be used to drive expression of a p53 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

Table 1 lists several elements/promoters that may be employed, in the context of the present invention, to regulate the expression of a gene. This list is not intended to be exhaustive of all the possible elements involved in the promotion of expression but, merely, to be exemplary thereof

TABLE 1

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |

TABLE 1-continued

Promoter and/or Enhancer

| Promoter/Enhancer | References |
| --- | --- |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

Further, selection of a promoter that is regulated in response to specific physiologic signals can permit inducible expression of the p53 construct. For example, with the polynucleotide under the control of the human PAI-1 promoter, expression is inducible by tumor necrosis factor. Table 2 provides examples of such inducible elements, which are regions of a nucleic acid sequence that can be activated in response to a specific stimulus.

The identity of tissue-specific promoters or elements, as well as assays to characterize their activity, is well known to those of skill in the art. Examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), human platelet endothelial cell adhesion molecule-1 (Almendro et al., 1996).

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) or chloramphenicol acetyltransferase (CAT) (prokaryotic) may be employed. Immunologic markers also can be employed. The selectable marker employed is not believed to be important, so long as it is capable of being expressed along with the polynucleotide

TABLE 2

Inducible Elements

| Element | Inducer | References |
| --- | --- | --- |
| MT II | Phorbol Ester (TFA)<br>Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x<br>poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 | encoding p53. Further examples of selectable markers are well known to one of skill in the art.

One will typically include a polyadenylation signal to effect proper ployadenylation of the transcript. The nature of the polyadenylation signal is not believed to be crucial to the successful practice of the invention, and any such sequence may be employed. Also contemplated as an element of the expression construct is a terminator. These elements can serve to enhance message levels and to minimize read through from the construct into other sequences.

In particular embodiments of the present invention, the expression construct comprises a virus or engineered construct derived from a viral genome. The ability of certain viruses to enter cells via receptor-mediated endocytosis and, in some cases, integrate into the host cell chromosomes, have made them attractive candidates for gene transfer into mammalian cells. However, because it has been demonstrated that direct uptake of naked DNA, as well as receptor-mediated uptake of DNA complexes (discussed below), expression vectors need not be viral but, instead, may be any plasmid, cosmid, or phage construct that is capable of supporting expression of encoded genes in mammalian cells, such as pUC or Bluescript™ plasmid series.

i. Adenoviruses

One of the preferred methods for in vivo delivery involves the use of an adenovirus expression vector. "Adenovirus expression vector" is meant to include constructs containing adenovirus sequences sufficient to (a) support packaging of the construct and (b) to express a protein or a polynucleotide (e.g., mRNA) that has been cloned therein.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m.u., is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

(Racher et al., 1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, a vector according to the present invention may be replication defective and, usually, will not have an adenovirus E1 region. Thus, it will may be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by (Karlsson et al., 1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

ii. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1998; Hersdorffer et al., 1990).

iii. Herpesvirus

Because herpes simplex virus (HSV) is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see (Glorioso et al., 1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotide reductase, a DNA polymerase, a ssDNA binding protein, a helicase/primase, a DNA dependent ATPase, dUTPase and others.

HSV genes from several groups whose expression is coordinately regulated and sequentially ordered in a cascade fashion (Honess and Roizman, 1974; Honess and Roizman, 1975; Roizman and Sears, 1995). The expression of α genes, the first set of genes to be expressed after infection, is enhanced by the virion protein number 16, or α-transducing factor (Post et al., 1981; Batterson and Roizman, 1983; Campbell et al., 1983). The expression of β genes requires functional a gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

iv. Adeno-Associated Virus

Recently, adeno-associated virus (AAV) has emerged as a potential alternative to the more commonly used retroviral and adenoviral vectors. While studies with retroviral and adenoviral mediated gene transfer raise concerns over potential oncogenic properties of the former, and immunogenic problems associate with the latter, AAV has not been associated with any such pathological indications.

In addition, AAV possesses several unique features that make it more desirable than the other vectors. Unlike retroviruses, AAV can infect non-dividing cells; wild-type AAV has been characterized by integration, in a site-specific manner, into chromosome 19 of human cells (Kotin and Berns, 1989; Kotin et al., 1990; Kotin et al., 1991; Samulski et al., 1991); and AAV also possesses anti-oncogenic properties (Ostrove et al., 1981; Berns and Giraud, 1996). Recombinant AAV genomes are constructed by molecularly cloning DNA sequences of interest between the AAV ITRs, eliminating the entire coding sequences of the wild-type AAV genome. The AAV vectors thus produced lack any of the coding sequences of the wild-type AAV, yet retain the property of stable chromsomal integration and expression of the recombinant genes upon transduction both in vitro and in vivo (Berns, 1990; Berns and Bohensky, 1987; Bertran et al., 1996; Kearns et al., 1996; Ponnazhagen et al., 1997a). Until recently, AAV was believed to infect almost all cell types, and even cross species barriers. However, it now has been determined that AAV infection is receptor-mediated (Ponnazhagen et al., 1996; Mizukami et al., 1996).

AAV utilizes a linear, single-stranded DNA of about 4700 base pairs. Inverted terminal repeats flank the genome. Two genes are present within the genome, giving rise to a number of distinct gene products. The first, the cap gene, produces three different virion products (VP), designated VP-1, VP-2 and VP-3. The second, the rep gene, encodes four non-structural proteins (NS). One or more of these rep gene products is responsible for transactivating AAV transcription. The sequence of AAV is provided by (Srivastava et al., 1983), and in U.S. Pat. No. 5,252,479 (entire text of which is specifically incorporated herein by reference).

The three promoters in AAV are designated by their location, in map units, in the genome. These are, from left to right, p5, p19, and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

v. Vaccinia Virus

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

vi. Lentiviral Vectors

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997), U.S. Pat. Nos. 6,013,516 and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc. and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

vii. Polyoma Viruses

The empty capsids of papovaviruses, such as the mouse polyoma virus, have received attention as possible vectors for gene transfer (Barr et al., 1979), first described the use of polyoma empty when polyoma DNA and purified empty capsids were incubated in a cell-free system. The DNA of the new particle was protected from the action of pancreatic DNase. Slilaty and Aposhian (1983) described the use of those reconstituted particles for transferring a transforming polyoma DNA fragment to rat FIII cells. The empty capsids and reconstituted particles consist of all three of the polyoma capsid antigens VP1, VP2 and VP3 and there is no suggestion that pseudocapsids consisting of only the major capsid antigen VP1, could be used in genetic transfer.

(Montross et al., 1991), described only the major capsid antigen, the cloning of the polyoma virus VP1 gene and its expression in insect cells. Self-assembly of empty pseudocapsids consisting of VP1 is disclosed, and pseudocapsids are said not to contain DNA. It is also reported that DNA inhibits the in vitro assembly of VP1 into empty pseudocapsids, which suggests that said pseudocapsids could not be used to package exogenous DNA for transfer to host cells. The results of (Sandig et al., 1993), showed that empty capsids incorporating exogenous DNA could transfer DNA in a biologically functional manner to host cells only if the particles consisted of all three polyoma capsid antigens VP1, VP2 and VP3. Pseudocapsids consisting of VP1 were said to be unable to transfer to exogenous DNA so that it could be expressed in the host cells, probably due the absence of $C^{2+}$ ions in the medium in which the pseudocapsids were prepared. Haynes et al. (1993) discuss the effect of calcium ions on empty VP1 pseudocapsid assembly.

U.S. Pat. No. 6,046,173, issued on Apr. 4, 2000, and entitled "Polyoma virus pseudocapsids and method to deliver material into cell," reports on the use of a pseudocapsid formed from papovavirus major capsid antigen and excluding minor capsid antigens, which pseudocapsid incorporates exogenous material for gene transfer.

2. Alternative Methods for Gene Delivery

The present invention may also employ non-viral gene transfer. This section provides a discussion of methods and compositions of non-viral gene transfer.

DNA constructs or the present invention are generally delivered to a cell, and in certain situations, the nucleic acid to be transferred may be transferred using non-viral methods.

Several non-viral methods for the transfer of expression constructs into cultured mammalian cells are contemplated by the present invention. These include calcium phosphate precipitation (Graham and Van Der Erb, 1973; Chen and Okayama, 1987; Rippe et al., 1990), DEAE-dextran (Gopal, 1985), electroporation (Tur-Kaspa et al., 1986), direct microinjection (Harlan and Weintraub, 1985), DNA-labeled liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, (Wong et al., 1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virue (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HJV and G-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous cell carcinoma (EP 0 273 085).

In other embodiments, the delivery vehicle may comprise a ligand and a liposome. For example, (Nicolau et al., 1987) employed lactosyl-ceramide, a galactose-terminal asialoganglioside, incorporated into liposomes and observed an increase in the uptake of insulin gene by hepatocytes. Thus, it is feasible that a nucleic acid encoding a therapeutic gene also may be specifically delivered into a cell type such as prostrate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a tumor suppressor gene may also be transferred in a similar manner in vivo and express the tumor suppressor gene.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into the animal. This may involve the surgical removal of tissue/organs from an animal or the primary culture of cells and tissues. Anderson et al., U.S. Pat. No. 5,399,346 and incorporated herein in its entirety, disclose ex vivo therapeutic methods. During ex vivo culture, the expression vector can express the p53 construct. Finally, the cells may be reintroduced into the original animal, or administered into a distinct animal, in a pharmaceutically acceptable form by any of the means described below.

E. COMBINATION WITH STANDARD CHEMO- AND RADIOTHERAPY

Tumor cell resistance to DNA damaging agents represents a major problem in clinical oncology. One goal of current cancer research is to find ways to improve the efficacy of chemo- and radiotherapy by combining it with protein or gene therapy. In the context of the present invention, it is contemplated that BZ or BZ-enhanced tumor suppressor gene therapy could be used similarly in conjunction with chemo- and radiotherapeutic intervention.

To kill cells, such as malignant or metastatic cells, using the methods and compositions of the present invention, one will contact a "target" cells with BZ or with the combination of BZ and a tumor suppressor protein or gene and, optimally, with at least one chemotherapeutic agent, e.g., a DNA damaging agent. These compositions would be provided in a combined amount effective to kill or inhibit proliferation of the cell. This process may involve contacting the cells with the BZ and the tumor suppressor protein or gene, and the chemotherapeutic agent(s) or factor(s) at the same time. This may be achieved by contacting the cell with a single composition or pharmacological formulation that includes both agents, or by contacting the cell with two distinct compositions or formulations, at the same time, wherein one composition includes the BZ or the BZ and the tumor suppressor gene, and the other includes the chemotherapeutic agent.

Alternatively, the BZ treatment may precede or follow the chemotherapeutic agent treatment by intervals ranging from minutes to weeks. In embodiments where the DNA damaging factor, and BZ and the tumor suppressor protein or gene are applied separately to the cell, one would generally ensure that a significant period of time did not expire between the time of each delivery, such that the DNA damaging agent and BZ and tumor suppressor protein or gene would still be able to exert an advantageously combined effect on the cell. In such instances, it is contemplated that one would contact the cell with both agents within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6, or 7) to several weeks (1, 2, 3, 4, 5, 6, 7 or 8) lapse between the respective administrations.

It is also conceivable that more than one administration of either BZ, and optionally the tumor suppressor protein or gene, or the chemotherapeutic agent will be desired. Various combinations may be employed, where BZ and optionally the tumor suppressor protein or gene is "A" and the chemotherapeutic or radiotherapetic agent is "B":

```
A/B/A    B/A/B    B/B/A    A/A/B    A/B/B    B/A/A
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A
A/B/B/B  B/A/B/B
```

The terms "contacted" and "exposed," when applied to a cell, are used herein to describe the process by which protein, such as BZ and tumor suppressor protein or gene, and a chemotherapeutic agent or factor are delivered to a target cell or are placed in direct juxtaposition with the target cell. To achieve cell killing, both agents are delivered to a cell in combined amount effective to kill the cell.

In particular, the present invention will employ DNA damaging agents as part of a combined therapy protocol. DNA damaging agents or factors are defined herein as any chemical compound or treatment method that induces DNA damage when applied to a cell. Such agents and factors include radiation and waves that induce DNA damage such as, γ-irradiation, X-rays, UV-radiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CCDP) and even hydrogen peroxide. The invention also encompasses the use of a combination of one or more DNA damaging agents, whether radiation-based or actual compounds, such as the use of X-rays with cisplatin or the use or cisplatin with etoposide. In certain embodiments, the use of cisplatin in combination with BZ and a tumor suppressor protein or gene is particularly preferred as this compound.

Any method also may be used to contact a cell with BZ and tumor suppressor protein or gene, so long as the method results in increased levels of functional tumor suppressor protein within the cell. This includes both the direct delivery of a tumor suppressor protein to the cell and the delivery of a gene or DNA segment that encodes the tumor suppressor gene, which gene will direct the expression and production of the tumor suppressor protein within the cell. In that protein delivery is subject to such drawbacks as protein degradation and low cellular uptake, it is contemplated that the use of a recombinant vector that expresses a tumor suppressor protein will provide particular advantages.

In treating cancer according to the invention, one would contact the tumor cells with a chemotherapeutic agent in addition to the BZ and tumor suppressor protein or gene. This may be achieved by irradiating the localized tumor site with DNA damaging radiation such as X-rays, UV-light, y-rays or even microwaves. Alternatively, the tumor cells may be contacted with the DNA damaging agent by administering to the subject a therapeutically effective amount of a pharmaceutical composition comprising a DNA damaging compound such as adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with BZ and the tumor suppressor protein or gene, as described above.

Agents that directly crosslink nucleic acids, specifically DNA, are envisaged and are shown herein, to eventuate DNA damage leading to a synergistic anti-neoplastic combination. Agents such as cisplatinum compounds, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally, or intraperitoneally.

Agents that damage DNA also include compounds that interfere with DNA replication, mitosis, and chromosomal segregation. Such chemotherapeutic compounds include adriamycin, also known as doxorubicin, etoposide, verapmil, podophyllotoxin, and the like. Widely used in clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake of neoplastic cells.

The skilled artisan is directed to "Remington's Pharmaceutical Sciences" 15$^{th}$ Edition, chapter 33, in particular pages 642-652. Some variations in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

The inventors propose that the regional delivery of BZ or BZ and tumor suppressor protein or gene to lung cancer cells in patients with p53-inked cancers will be an efficient method of delivering a therapeutically effective protein to counteract the clinical disease. Similarly, the chemo- or radiotherapy may be directed to a particular, affected region of the subject's body. Alternatively, systemic delivery of BZ or BZ and tumor suppressor protein or gene, or the DNA damaging agent may be appropriate in certain circumstances, for example, where extensive metastasis has occurred.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Chemicals

Methyl 5-benzoylbenzimidazole-2-carbamate (Mebendazole (MZ)) and methy 5-(phenylthio)-2-benzimidazole-2-carbamate (Fenbendazole (FZ)) were purchased from Sigma Chemical Company (St. Louis, Mo.). All other chemicals were purchased from Sigma unless otherwise indicated.

Cell Lines

All non-small cell lung cancer (NSCLC) cell lines except A549 were gifts from Drs. Adi Gazdar and John Minna (The University of Texas Southwestern Medical Center, Dallas, Tex.). All other cell lines were obtained from the American Type Culture Collection (Rockville, Md.). Cell lines were grown according to the directions provided by suppliers. All media were supplemented with 10% heat-inactivated fetal bovine serum (Life Technologies, Inc.) and antibiotics (100 mg/ml of streptomycin/ml and 100 I.U. of penicillin/ml; Life Technologies, Inc.). MZ and FZ were dissolved in dimethylsulfoxide (DMSO) and then diluted in phosphate-buffered saline (PBS) (1:1). When reagents containing DMSO were used, an equal volume of DMSO were added to the control cells.

In Vitro Cell Culture and Proliferation Assay

All cell lines were grown in RPMI 1640 medium supplemented with 5% fetal bovine serum and 5% $CO_2$. All experiments were done when the cells were 70% confluent. For cell growth measurements, $5\times10^4$ cells were plated in each well of six-well plates. Control and BZ-treated (0.05 µg/ml) cells were trypsinized and counted using a hemocytometer. Experiments were done in triplicate and the mean and standard deviation were determined by standard methods. Using the Curve Fit 1.3 program, the 50% growth inhibitory concentrations ($IC_{50}$) were extrapolated from a plot of the percent control cell growth (triplicate determinations) versus drug concentration after 24 h of treatment.

RNA Isolation and Northern Blot Analysis

Total RNA was isolated from the subconfluent cultures using the guanidinium thisocyanate method (Lacey, 1988). After this 20 µg of the RNA was electrophoresed in a denaturing 1.2% agarose/morpholinepropanesulfonic acid (MOPS)-formaldehyde gel, transferred onto a nitrocellulose membrane, and hybridized to a $^{32}$P-radiolabeled p53 cDNA probe, as described elsewhere (Lubiga and Prichard, 1990). The $^{32}$P-labeled probes were generated using random primers (>$8\times10^8$ cpm/µg). Blots were washed at 65° C. in 2× standard saline citrate (SSC) for 30 min and then washed twice at 60° C. in 0.1% sodium dodecyl sulfate (SDS) and 0.1×SSC. The cDNA probes used were 1.2-kb human p53 cDNA and an 800-bp fragment of human p21 cDNA.

Antibodies

The following antibodies were used: mouse anti-p21 monoclonal antibody WAF-1 (Ab-1), Oncogene Sciences (Cambridge, Mass.); mouse monoclonal anti-Cyclin A (Sigma, St. Louis, Mo.), rabbit anti-human cyclin D (Upstate Biotech, Inc.), mouse anti-RB monoclonal antibody (Pharmigen, San Diego, Calif.), and mouse anti-c-myc monoclonal antibody (Invitrogen, Carlsbad, Calif.). Mouse anti-BCL-2 (100) monoclonal antibody, rabbit anti-Bcl-$X_L$ (S-19) polyclonal antibody, rabbit anti-Bax (N-20) polyclonal antibody, mouse anti-MDM2 (SM P14) monoclonal antibody, mouse anti-2 (100) monoclonal antibody, mouse anti-p52 Bp53-12) monoclonal antibody, mouse anti-Cdk2 (M2-G) goat polyclonal antibody, and mouse anti-Cdc-2 p34 (17) monoclonal antibody were all purchased from Santa Cruz Biotechnology (Santa Cruz, Calif.). Horseradish peroxidase-conjugated anti-mouse IgG and anti-rabbit IgG were purchased from Amersham International (Arlington Heights, Ill.).

Nuclear Staining Assay

Cells were seeded onto chamber slides and treated with various reagents, after which cell monolayers were washed twice with ice-cold PBS (pH 7.4). Thereafter, cells were fixed for 5 min at 20° C. in 10% formalin. The washing step with PBS was then repeated once. To stain the nuclei, the cells were incubated for 10 min with 10 µg/ml of Hoechst 33342 and then washed with PBS. The coverslips with the stained cells were mounted in 80% glycerol in PBS containing 1 mg/ml P-phenylenediamine and examined with a Nikon epifluorescence microscope.

Apoptotic Assay and TdT FACS Analysis

Apoptotic assay was done using M30 CytoDEATH apoptotic cell death assay kit (Boehringer Mannnheim). Cells were grown on chamber slides, control and benzimidazole treated cells were stained with Mouse monoclonal antibody (clone M30) as per manufacturer's instructions. Apoptotic cells were examined with a Nikon microscope and photomicrographed. For TdT FACS analysis control and treated cells were collected by trypsinization, washed in PBS, and fixed overnight in 70% ethanol. The next day, cells were rehydrated in PBS for 30 min, centrifuged, and resuspended in PBS. For DNA analysis, propidium iodide (PI) was added at 50 µg/ml, and the cells were incubated in the presence of RNase A (15 mg/ml for 30 min at 37° C.). To detect DNA strand breaks associated with apoptosis, cells were fixed in 1% formaldehyde for 15 min at 4° C., rinsed in PBS, and stored at 4° C. in ice-cold 70% ethanol. Before staining, the cells were washed in PBS, and $10^6$ cells were resuspended in 50 ml of cacodylated buffer containing 100 µ/ml TdT enzyme and 0.5 nM biotin-16 dUTP for 30 min at 37° C. Cells were washed in PBS and resuspended in 100 ml of 4×SSC containing 2.5 mg/ml fluoresceinated avidin, 0.1% Triton X-100, and 5% dry fat milk and then incubated at room temperature for 30 min in the dark. Finally, cells were washed in PBS and resuspended in PI buffer. Flow cytometry was carried out in a fluorescence-activated cell sorter (Epics Elite; Coulter, Inc., Hialeah, Fla.).

Immunohistochemical Staining

Cells were seeded onto glass coverslips and fixed as described above. The cells were blocked at 37° C. for 30 min with 2% bovine serum albumin, 5% fetal bovine serum, and 5% normal goat serum in PBS. The cells were then incubated at room temperature for 45 min with anti-p53 (Ab-2) antibody (1:1000 dilution) in blocking buffer and washed with PBS. The cells were then incubated with HRP-conjugated goat anti-mouse IgG secondary antibody (Amersham). After washing, the immunocomplex was detected by an avidin-biotin complex kit, and slides were mounted as described above.

Cell Lysates and Immunoblotting

Cells were grown in 6-cm dishes, cultured, and treated as described above. To prepare the whole-cell lysates, the medium was removed and cells were washed twice with ice-cold Tris-buffered saline (TBS) (150 mM NaCl, 10 mM Tris; pH 7.6) and lysed with 0.5 ml of lysis buffer (10 mM Tris, 150 mM NaCl, 1% Triton X-100, 5 mM EDTA, 25 mM glycerphosphate, 1 mM phenylmethylsulphonyl fluoride (PMSF), 2 mM benzamidine, 10 mg/ml aprotinin, 10 mg/ml leupeptin, and 1 mM sodium orthovanadate) for 15 min. The lysed cells were then transferred to 1.5 ml microtubes, centrifuged at 15,000×g for 10 min at 4° C., and the supernatants collected mixed with Laemmli's sample buffer and subjected to western blot analysis as described elsewhere (Nare et al., 1994). Blots were probed with anti-p53 monoclonal antibody Bp53-12 (Santa Cruz Biotechnology, Inc.) and the immunocomplex was detected by the Enhanced Chemiluminescence kit according to the manufacturer's directions (Amersham). Blots were then reprobed, this time with anti-actin monoclonal antibody (Amersham), to show that protein loading was equal.

Pulse-Chase Experiments

Cells were treated with 0.05 µg/ml fenbendazole or mebendazole for 24 h. After this, control (mock-treated) and drug-treated H460 cells were incubated with 10 µg/ml cycloheximide in drug-free medium for different times and then processed to obtain total cell extracts. Finally, samples were denatured by boiling them in SDS-loading buffer (100 mM Tris, pH 6.8; 2% SDS; 0.1% bromphenol blue; 10% glycerol; 25 µM β-mercaptoethanol) and loaded onto a 10% SDS-polyacrylamide gel. Blots were probed with anti-p53 monoclonal antibody B p53-12 (Santa Cruz Biotechnology, Inc.) and anti-actin monoclonal antibody (Amersham). The immunocomplexes were detected using the Enhanced Chemiluminescence kit according to the manufacturer's directions as described above. The intensities of the bands were quantitated with a PhosphoImager using ImageQuant™ Software (Molecular Dynamics, Sunnyvale, Calif.).

Example 2

Results

BZ-Induced Apoptosis in Human NSCLC Cell Line H460

The inventors tested the effect of BZ treatment on the human NSCLC cell line H460. H460 cells were treated with FZ, (0.05 µg/ml) or MZ (0.5 µg/ml) and the morphological changes associated with apoptosis were identified. Widespread loss of viability was noted by gross examination of the cells at 24 and 48 hrs after treatment using a phase-contrast light microscope. After treatment for 48 h, the cells became rounded and loosely attached to the plate, suggesting the cells were losing viability. Further analyses of the cell samples showed that the cells were undergoing apoptosis. Most of the morphological hallmarks associated with apoptosis were detectable, including cell shrinkage, DNA fragmentation and chromatin condensation. Chromatin condensation was noted under a fluorescence microscope at 24 h after treatment, by staining the nuclei with Hoechst 33342 fluorescent dye. The DNA strand breaks typical of the apoptosis were also demonstrated by TUNEL and benzimidine staining (FIG. 1A). The morphological changes produced by FZ and MZ treatments were indistinguishable. Gross morphological changes associated with a loss of viability were observed by 24 hr post-treatment, whereas signs of apoptosis, detected by DNA staining and TUNEL assays, became apparent by 24 hr after drug treatment.

Induction of Nuclear Accumulation of p53

Both FZ and MZ showed an apoptotic effect on the H460 cells. To rule out the possibility that FZ and MZ have an effect on other proteins known to have a role in various apoptotic pathways, the inventors evaluated the effect of these drugs on a panel of such proteins. Many of these proteins are known activators or suppressors (e.g., Bcl-2, Bax, Rb) of apoptosis and have already been shown to be expressed in these cells. Specifically, the levels of these proteins were evaluated by Western blot analyses before and after exposure to 0.05 µg/ml FZ or MZ for 24 hr using whole-cell extracts. Although the levels of nuclear p53, p21 and MDM2 were enhanced, interestingly, there were no changes in the levels of Bcl-2, Cyclin A, Cyclin D, Cdc 2, Bcl-$X_L$, Bax, Rb and Cdk-2. The protein level of the phosphorylated form of Rb also remained unchanged after treatment.

Because FZ and MZ specifically induced the formation of nuclear p53 in the H460 cell line, the apoptotic effect of these drugs on these NSCLC cells is presumably p53-dependent. H460 cells were treated with FZ or MZ for 24 hr (0.05 µg/ml), and the proteins from both control and treated cells was analyzed for p53 protein and p53 target gene expression. There was also a positive correlation between the ability of FZ and MZ to induce apoptosis and the ability of these agents to mediate the nuclear accumulation of p53. As a result of p53 accumulation, the p53-regulated genes were also expressed at a much higher level. By Western blot analysis increased p53 expression correlated with enhanced p21 and MDM2 protein levels. Because of the close structural resemblance between FZ and MZ (i.e., both have the benzamidazole core structure), it is not surprising that they both induced apoptosis and the nuclear accumulation of p53.

Kinetics of Induction of p53 and Apoptosis

Cell extracts were prepared from H460 cells exposed to 0.05 µg/ml FZ or MZ for various durations (1 to 24 hr). The effect of FZ and MZ on the nuclear accumulation of p53 appeared to be gradual and was not significant within the first hour of exposure. However, it became significantly detectable at about 16 hr and peaked at 24 hr. The appearance of p53 in response to drug treatment also coincided with the initiation of apoptosis, which was detectable by 24 hr, as well as shown earlier by TdT FACS analysis. Northern blot analysis of p53 mRNA levels in H460 cells treated with 0.05 µg/ml FZ or MZ after 24 hr of treatment however, revealed no significant changes in the p53 mRNA levels, indicating that the nuclear accumulation of p53 was not due to an increase in p53 transcripts. As proof that the p53 induced in these cells was functional, the level of the transcript for one of the p53 target genes, p21/WAF1, was assessed and found to be significantly increased at the time the p53 level peaked. Total RNA was extracted and 20 µg/ml per lane was used for the analysis. p53 protein was detected by immunoblot analysis.

The induction of p53 became detectable at 0.01 µg/ml FZ. However, the induction appeared to occur abruptly, by which suggests the presence of a cooperative mechanism. Similar observations were made under serum-free conditions, and this suggests that the source of the cooperative effect is not a factor in the serum. As predicted from the Northern blot experiment, the steady state p21 level did indeed increase significantly over that in the control experiment, in parallel with the increase in the p53 protein level, in the H460 cells (wild-type p53) but not in the H322 cell line, which has mutant p53. The results of the DNA fragmentation assay, which assessed the effect of FZ in inducing apoptosis, and the nuclear accumulation of p53 correlated well in the H460; H322 and H1299 (p53 deleted), NSCLC cell lines tested.

Increased Half-Life of p53 in Drug-Treated Cells

Because FZ and MZ did not seem to affect the transcriptional rate of the p53 gene, the inventors evaluated the effect of these agents on the stability of p53 in H460 cells and noted that both agents were able to prolong the half-life of the p53 protein in H460 cells. H460 cells were treated with 0.05 µg/ml FZ for 24 hr, and then both untreated control and treated cells were washed with PBS and treated with 24 µg/ml cycloheximide. After that, cells were harvested at different times. The total cell protein was extracted and analyzed on a 10% polyacrylamide-gel, followed by Western blot analysis using p53 and actin monoclonal antibodies. Actin, in the Western blot, served as an internal control. The experiment was repeated twice, with similar results.

Because the results were similar between FZ and MZ treatments, only data obtained with FZ treatment are presented. Specifically, the half-life of the wild-type p53 in treated H460 cells was about 6-8 hr, but increased dramatically to 24 hr in the drug-treated cells (FIG. 2). The former finding is consistent with that in previous reports of the half-life of p53 in a number of cancer cell lines, as opposed to the 20- to 30-min half-life seen in normal fibroblasts (Freedman et al., 1998). Data from the pulse-chase experiments were quantitated with a PhosphoImager using ImageQuant™ software. Circles and triangles represent data from FZ-treated and control samples, respectively.

Selective Induction of Apoptosis by Fenbendazole and Mebendazole in Tumor Cells Carrying Wild-Type p53

Studies to determine the $IC_{50}$ for fenbendazole and mebendazole were performed on a panel of six different human cancer cell lines: two carrying the wild-type p53 gene and actively expressing the p53 protein, (H460 and A549); one marked by homozymes deletion of the p53 gene and lacking p53 gene expression (H358); two expressing mutant p53 (H322 and H596); and one in which wild-type p53 is inactivated by human papilloma virus E6 protein. Comparison of the concentrations of bendimidazoles necessary to inhibit the growth of the different cell lines by 50% ($IC_{50}$) indicated that wild-type p53 containing cell lines were 2- to 7-fold more sensitive than the p53-mutated or deleted cell lines (Table 2). A dose of 166 nM (~0.05 mg/ml) was chosen for these studies because it had been shown previously that this concentration was sufficient to induce wild-type p53 after 24 h of treatment.

TABLE 3

Sensitivity of cancer cell lines to bendimidazoles

| Phenotype and cell lines | $IC_{50}$ | |
|---|---|---|
| | Fenbendazole (nM) | Mebendazole (nM) |
| p53 positive | | |
| H460 | 152 | 106 |
| A549 | 123 | 130 |
| HeLa (p53 inactivated) | 853 | 400 |
| p53 mutated | | |
| H322 | 816 | 871 |
| H596 | 643 | 601 |
| p53 deleted | | |
| H358 | 654 | 893 |

[a]Concentrations of drugs (in nanomolars) required to inibit growth by 50% after 1 day of exposure.

Figure 3A:
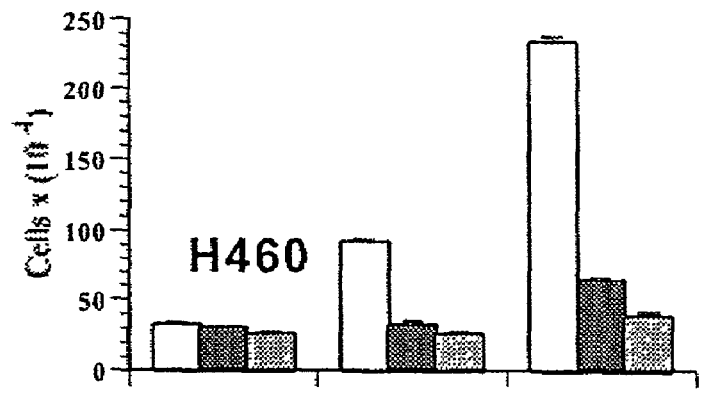
FIGS. 3A-3C: Effect of FZ and MZ with the Induction of the Cell Growth and Nuclear Accumulation of Wild-Type p53 Protein. The NSCLC cell lines studies in this experiment consisted of the wild-type p53-containing human lung cancer cell lines H460 (FIG. 3A), the mutant p53 cell line H322 (FIG. 3B), and the p53 deleted H1299 cell line (FIG. 3C). Cells were exposed to FZ (filled bar) or MZ (hatched bar) for 24 hr. The values shown are the means ±standard deviation of triplicate samples.
Figure 3B:
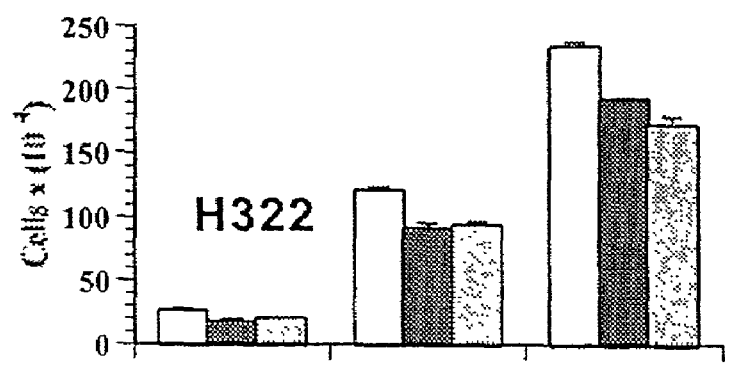
Figure 3C:
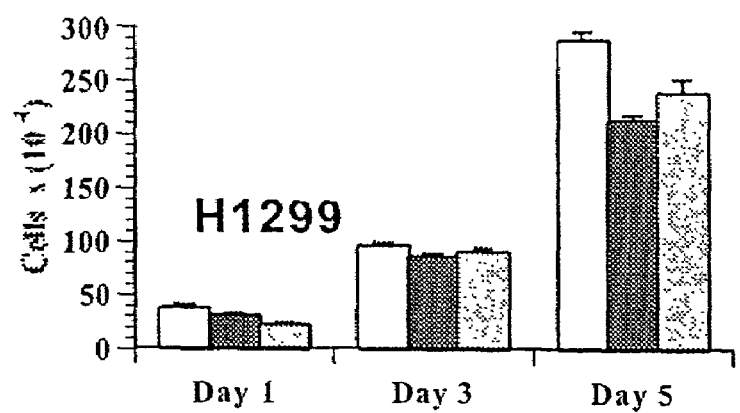

To further investigate the relationship between the induction of functional p53 and the subsequent apoptosis mediated by these drugs, the inventors posited that if BZs require wild-type p53 in order to exert their effect, then fenbendazole and mebendazole would not be cytotoxic to the many tumor lines producing a mutated p53 protein. To investigate this possibility, human cell lines derived from NSCLC origins of differing p53 status were further analyzed by a 5-day cell growth assay. The cells were plated onto a six-well plate, and the viability of the cells was determined by trypan blue exclusion. Cells were counted on a hemocytometer. The values shown are the means ±standard deviation of triplicate samples. Duplicate experiments gave similar results. Results for three cell lines (H460, H322, H1299) are shown in FIG. 3. H322 is a human lung adenocarcinoma line that produces a mutant p53 protein. The mutant p53 protein is generally more stable (20,21) and this was reflected in the present case by the presence of higher amounts of the p53 protein in the nucleus of H322 cells prior to drug treatment (FIG. 3). H11299 is a p53 gene-deleted human NSCLC cell line and does not express any p53 protein. However, fenbendazole and mebendazole induced nuclear accumulation of p53 only in the H460 cell line, which carries wild-type p53 genes. Fenbendazole and mebendazole therefore appeared to be significantly effective in killing wild-type p53-containing cancer cells. Cells were exposed to FZ (filled bar) or MZ (hatched bar) for 24 hr. A concentration of 0.05 µg/ml FZ and MZ was used. An immunoblot analysis of nuclear p53 was also performed to determine whether these drugs induced the production of p53. Equal amounts of protein extracts from each cell line before and after treatment were used for this analysis.

An analysis of 18 human tumor cell lines (Table 4) was performed, which showed that these drugs had an effect on nuclear accumulation of p53 only in the cell lines carrying the wild-type p53 gene. Both drugs induced some degree of growth inhibition; rather than apoptosis, in cell lines that contained mutated or deleted p53; however, they induced greater growth inhibition in cell lines containing wild-type p53: As expected, HeLa and SiHa cervical cancer cell lines containing wild-type p53 along with HPV-E6 protein were less sensitive to the inductive effect of these drugs on apoptosis and p53 accumulation.

Figure 4A:
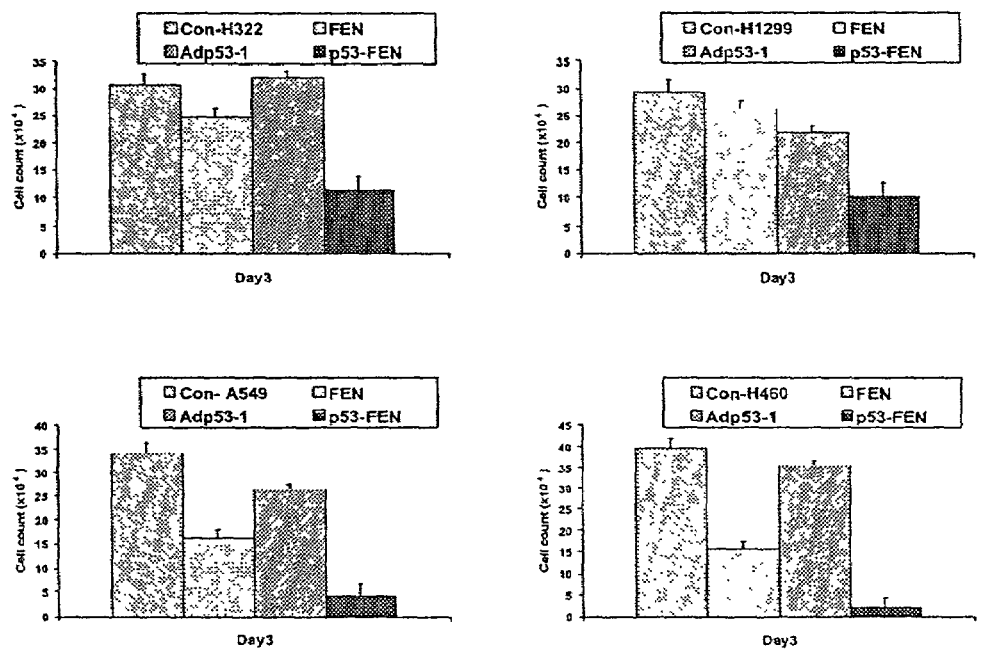
FIGS. 4A-4C: Synergistic Effect of Ad5p5 and FZ. Approximately $10^4$ cells were seeded on tissue culture plates 24 h before drug treatment or adenoviral infection.

In order to further confirm that bendamidazoles works through p53 mediated pathway the synergistic effect of Ad5p53 and Fenbendazole on tumor cell growth was examined in four human lung cancer cell lines that differed in p53 status but were all <transduced with Ad5p53: H1299 (p53 deleted), H322 (p53 mutated), H460 (wt p53) and A549 (wt p53). Because the initial dose-response studies indicated that 0.05 µg/ml FZ induced high levels of wt p53 protein expression in H460 cells without toxicity, the inventors used this concentration for all the proliferation assays. In those assays, growing, cultured cells were trypsinized and plated ($10^4$ cells/well) and then infected the next day with Ad5p53 at 1 MOI. Viral supernatant was then added, after which cells were incubated for 24 h, washed with PBS, fed fresh medium or incubated with medium containing FZ for 24 h, washed again, and fed fresh medium. In contrast, uninfected cells (controls) were treated with FZ for 24 h, washed with PBS, fed fresh medium, and then subjected to a 3-day growth assay (FIG. 4A).

Figure 4B:
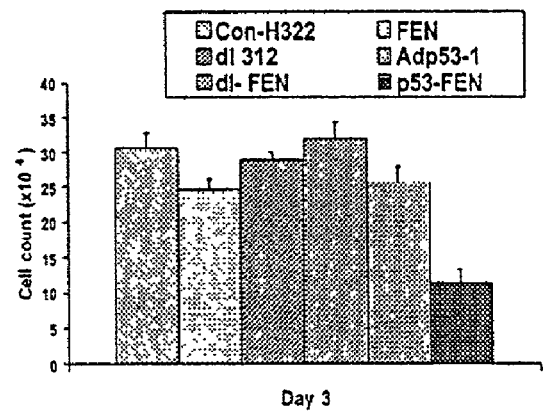
Figure 4C:
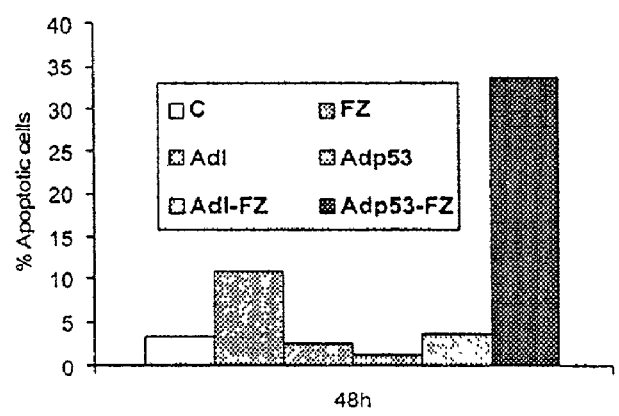

Our experimental results indicated that dl312 (empty vector) had no effect in combination with FZ (FIG. 4B). When the four lung cancer cell lines were transiently infected with 1 MOI Ad5p53 for 24 h, no growth suppression was observed, regardless of p53 status. When all four lines were treated with FZ alone for 24 h, the p53-mutated and deleted cells were not growth inhibited, whereas the wt p53H460 cells was significantly so. However, a striking growth inhibition was observed in all four cell lines when the Ad5p53-transduced cells (1 MOI, 24 h) were treated with FZ for 24 h and were grown in normal medium for a 3-days growth assay. These findings suggest that transducing of Adp53 will induce efficient p53-mediated killing of tumor cells in the presence of p53 super-induction by FZ. The A549 cells (containing wt p53) showed 11% apoptotic cells following FZ treatment. Low dose wild-type Adp53 had no apoptotic effect, whereas the A549 cells showed 30% apoptotic cells death 48 h after combination treatment, as shown by terminal deoxynucleotidal transferase (TDT) staining analysis via fluorescence-activated cell sorting (FACS) as shown in FIG. 4C. These results suggest that FZ works though a p53 dependent pathway.

Inhibition of Apoptotic Effect by the Dominant Negative Factor E6

To provide more direct evidence that the cytotoxic effect of fenbendazole and mebendazole correlates with the availability of functional p53 in the cell, the inventors studied HeLa and SiHa ovarian cancer cells line that produce the E6 protein, which acts as a dominant negative factor for wild-type p53. This production of E6 is attributable, at least in part, to a dominant negative mechanism involving the degradation of the endogenous wild-type molecule. In this experiment, the HeLa (HPV-18) and SiHa (HPV-16) cells were treated with fenbendazole for 48 h, and the total cell proteins were subjected to immunoblot analysis for p53 protein production. However, no induction of p53 production was observed, suggesting that the E6-mediated degradation of p53 was utilizing a path different from that used in normal cells. Because these results could also have been due to a decrease in the MDM2 protein level after fenbendazole treatment, the inventors reprobed the membrane with MDM2 monoclonal antibody. However, MDM2 protein production remained low in both control and fenbendazole-treated HeLa and SiHa cells, whereas MDM2 production in the H460 cells increased several times with the increase in the p53 protein levels. Further, in these dominant negative lines, the level of the p21 protein did not increase above the base level after treatment with these drugs. This clearly showed that fenbendazole-mediated cell killing had become less effective in cells producing the wild-type p53-inactivating E6 protein, thereby limiting the ability of fenbendazole and mebendazole to mediate apoptosis. This finding may, in part, explain why killed those cells containing wild-type p53. However, one cannot rule out the possibility that a pathway other than the p53 pathway is also involved in the cytotoxic effect of these drugs.

TABLE 4

Effect of FZ and MZ on p53 Induction and Apoptosis in Human Tumor Cell Lines Differing in p53 Status

| Cell Line | Tumor origin | P53 status | % Cell Viability[a] fenbendazole[b] | mebendazole[b] | Nuclear p53 | p53 Induction |
|---|---|---|---|---|---|---|
| MCF-7 | Breast | Wild-type (31)[c] | 43.88 ± 7.3 | 24.26 ± 8.4 | No | Yes |
| H460 | Lung | Wild-type (32)[c] | 39.16 ± 6.4 | 25.23 ± 7.6 | Yes | Yes |
| H549 | Lung | Wild-type (32)[c] | 46.43 ± 13.3 | 39.19 ± 10.7 | Yes | Yes |
| H322 | Lung | R248H (32) | 65.92 ± 4.9 | 68.50 ± 3.7 | Yes | No |
| H596 | Lung | R245C (32) | 86.71 ± 11.5 | 86.19 ± 8.0 | Yes | No |
| H226Br | Lung | R254 (33) | 80.06 ± 11.1 | 64.24 ± 0.2 | Yes | No |
| H1299 | Lung | Deleted (32) | 89.17 ± 1.1 | 89.18 ± 4.3 | No | No |
| H358 | Lung | Deleted (32) | 88.35 ± 17.8 | 73.45 ± 1.8 | No | No |
| Saos-2 | Osteosarcoma | Deleted (34) | 76.48 ± 5.9 | 65.36 ± 10.1 | No | No |
| Hep 3B | Liver | Deleted (35) | 79.49 ± 12.5 | 83.24 ± 1.5 | No | No |
| SW480 | Colon | R273H (36) | 70.59 ± 7.6 | 63.63 ± 13.3 | Yes | No |
| MDA 231 | Breast | R280K (37) | 65.26 ± 5.0 | 66.24 ± 15.8 | Yes | No |
| SK-OV-433 | Ovarian | Wild-type (38)[c] | 52.52 ± 13.2 | 28.15 ± 6.1 | Yes | Yes |
| HeLa | Cervical | Wild-type but inactivated by E6 (37)[c] | 93.63 ± 7.4 | 92.42 ± 6.27 | Yes | No |
| SiHa | Cervical | Wild-type but inactivated by E6 (39)[c] | 94.52 ± 7.4 | 91.32 ± 8.6 | Yes | No |

TABLE 4-continued

Effect of FZ and MZ on p53 Induction and Apoptosis in Human Tumor Cell Lines Differing in p53 Status

| Cell Line | Tumor origin | P53 status | % Cell Viability[a] | | Nuclear p53 | p53 Induction |
| --- | --- | --- | --- | --- | --- | --- |
| | | | fenbendazole[b] | mebendazole[b] | | |
| RD | Rhabdomyosarcoma | R248W (40) | 78.73 ± 12.0 | 72.24 ± 2.8 | Yes | No |
| HT1080 | Osteosarcoma | Wild-type (41)[c] | 54.52 ± 12.0 | 44.49 ± 7.7 | ND[d] | ND[d] |

[a]The viability of the cells was measured by trypan blue extrusion cell count assay. The 100% value was derived from measurements obtained from untreated cells. Experiments were done in triplicate. p53 protein was examined by immunoblot analysis of the nuclear extracts isolated from each cell line before and after treatment with 0.05 mg/ml fenbendazole and mebendazole for 24 h.
[b]Concentration of fenbendazole and mebendazole = 0.05 mg/ml.
[c]This cell line carries a wild-type allele.
[d]ND, not done.

Example 3

Materials and Methods

In Vitro Cell Culture and Proliferation Assay

Cells of the human non-small cell lung cancer (NSCLC) cell line A549, WI-38 normal fibroblast (American Type Culture Collection, Rockville, Md.) and H460 (a gift from Drs. Adi Gazdar and John Minna. University of Texas Southwestern Medical Center, Dallas) were seeded on culture plates ($2 \times 10^4$ cells/well) in F12 and RPMI medium, respectively, supplemented with 10% heat-inactivated fetal calf serum and antibiotics. HUVEC were grown in medium supplemented with growth factor (Clonetics, San Diego). The cells were then exposed to MZ dissolved in dimethyl sulfoxide (DMSO) when grown to 40-50% confluence. Cell growth was monitored by counting the cells using a hemocytometer.

In Vivo Tumor Growth in Nu/Nu Mice

Mice that had received 3.5 Gy of total body irradiation 1 day before inoculation were given injections into the shoulder of $2 \times 10^6$ tumor cells. Mice were then given MZ oral suspension (100 mg Vermox chewable tablet, Janssen Pharmaceutica, NJ, suspended in 10 ml PBS by sonication for 30 sec) with indicated concentration every other day, starting the day after 3-5 mm tumor established. Five mice were used in each group. Control and treated mice were then monitored for tumor growth; the tumors were measured externally in cross-sectional diameter every 7 days. Tumor volumes were calculated as previously described. Experiments were repeated three times.

Evaluation of Lung Metastases and Treatments In Vivo

To establish lung metastases, female nude mice were injected intravenously via tail vein with $10^6$ A549 tumor cells suspended in 200 ml of sterile PBS. Six days later, mice were divided into two groups of 5 mice each and treated. Group 1 received no treatment and group 2 received the experimental MZ drug orally at 1 mg of drug (100 µl) twice a week for 3 weeks. After 3 weeks, animals were euthanized by $CO_2$ inhalation. Lungs from each of the mice from the two groups were injected intra-tracheally with India ink and fixed in Feketes solution. The therapeutic effect of MZ treatment was determined by counting the number of metastatic tumors in each lung under a dissecting microscope without knowledge of the treatment groups. The experiments were performed three times and data analyzed and interpreted as statistically significant if the p value was <0.05 by the Mann-Whitney rank-sum test.

Immunohistochemical Analysis

Subcutaneous H460 tumors established in nu/nu mice that were either not treated or treated with MZ were harvested and fixed in 4% buffered formalin, paraffin embedded, and cut as 6 mm thick sections. Tissue sections were stained for CD31 expression using rat anti-mouse CD31 antibody (Pharmingen) as previously described with slight modifications. Briefly, following deparafinzation and rehydration, tissue sections were treated with 0.3% $H_2O_2$ in methanol for 30 min to block endogenous peroxidase activity and were subsequently incubated with normal rat serum for 30 min at room temperature. Following incubation, slides were treated with protease for 15 min followed with rat monoclonal anti-CD31 antibody (1:1000 dilution) for 60 minutes. After 30 min incubation with anti-rat secondary antibody (provided with ABC kit, Vector) CD31 in tissues was detected with DAB by enhancement with avidin-biotin reaction ABC kit. The slides were counterstained with hematoxylin and then mounted with Aqua-mount (Lerner Labs, Pittsburgh, Pa.). The number of vascular areas staining positive for CD31 were analyzed under bright-field microscopy. A total of at least five fields per specimen were analyzed. In all the staining procedures, appropriate negative controls were included.

Angiogenesis by Tumor Cells In Vivo

In vivo angiogenesis was assayed by the dorsal air-sac method (Bouvet et al., 1998). Briefly, $1 \times 10^7$ cultured A549 cells were suspended in PBS and packed into round cellulose ester membrane chambers with a diameter of 14 mm (pore size, 0.45 µm; Millipore, Bedford, Mass.). The chambers were then implanted into a dorsal air sac of a nude mouse. After the chamber implantation mice were fed with MZ oral suspension (1 mg/mouse/day). Five mice were used in each group. The mice were killed on day 5, and the subcutaneous region overlying the chamber in each mouse was photographed. The experiment was repeated two times with identical results.

Statistical Analysis

Descriptive statistics such as mean and standard deviation were reported to summarize the study results. Two-sample t-test was performed to compare tumors of control and treated under various conditions.

Example 4

Results

Figure 5A:
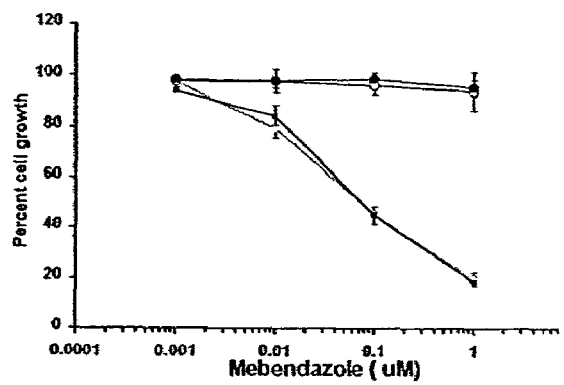
FIGS. 5A-5D: Effect of mebendazole on cell growth and tumorigenesis.

Initially, the inventors examined the effect of MZ on proliferation of human lung cancer cell lines (H460 and A549) in vitro. A 24 h treatment strongly inhibited growth of the lung cancer cell lines (FIG. 5A), the half maximal inhibitory concentration (IC$_{50}$) being ~0.12 µM. Interestingly, it had no effect on normal fibroblast or human vascular endothelial cells (HUVEC). The growth inhibitory effect was not restricted to lung cancer cells, as MZ profoundly inhibited growth of breast, ovarian and colon carcinoma and osteosarcoma producing IC$_{50}$ that varied from 0.1 µM and 0.8 µM. Table 5 shows the growth inhibition of a number of tumor cell lines after 24 h of MZ treatment at a 0.16 µM concentration. While MZ was highly cytotoxic (reducing of cells below the initial plating density) to the tumor cells in culture, it did not show any effect on normal HUVEC or MJ90 fibroblast cells.

Figure 5B:
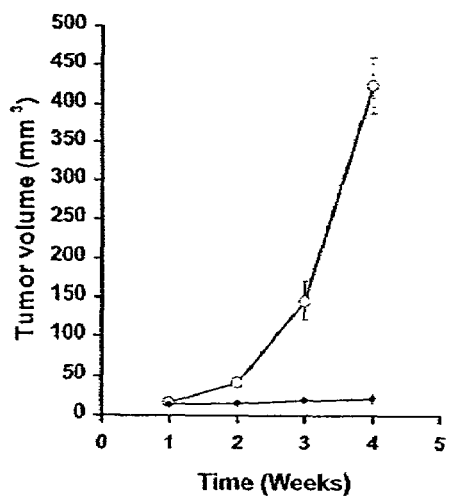
Figure 5C:
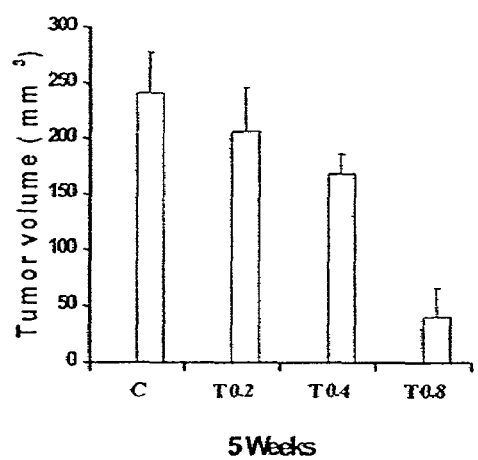
Figure 5D:
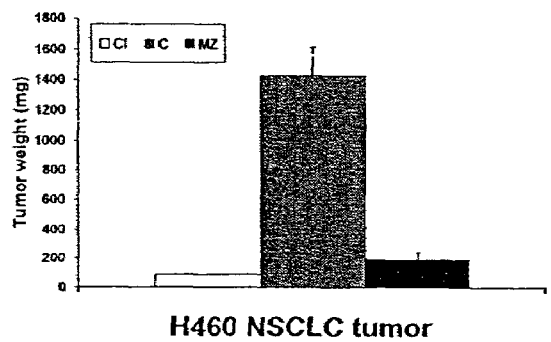

The in vitro effect of MZ on proliferation of tumor cell lines prompted us to investigate its antitumor activity in an athymic nu/nu mouse model. Tumors were established by subcutaneous injection of H460 cells, a human non-small cell lung cancer (NSCLC) cell line (2×10$^4$ cells/mouse) (FIG. 5B). Mice with established tumors (3 mm in diameter) were fed orally with 1 mg of MZ every other day, which was sufficient to profoundly inhibit tumor growth. Moreover, 10/10 animals inoculated with 1×10$^6$ cells developed tumors within 12 days. A dose escalation study indicated that MZ suppressed the growth of the tumors in a dose-dependent manner. T0.2, T0.4 and T0.8 correspond to 0.2, 0.4 and 0.8 mg of MZ treatment groups (FIG. 5C). Animals with established tumors, 3-5 mm in diameter, received MZ every other day for 4 weeks, after which tumors were harvested, photographed, and weighed. There was a marked difference in the tumor weight between MZ-treated and control animals (FIG. 5D). The xenograft of H460 cells in nu/nu mice exhibited a marked increase in tumor growth kinetics compared with MZ treated group. The treated mice showed no signs of toxicity and were all healthier than the control mice group during these 4 weeks of treatment period.

To determine whether the observed differences in growth kinetics in vivo were associated with variation in tumor vascularity, the inventors subjected tumors established from the H460 cells to immunohistological analysis using an antibody against CD31. The analysis demonstrated significantly increased blood vessel density in control untreated mice compared with the MZ-treated group. MZ had profoundly reduced the nasovascularization and growth of human lung cancer xenografts in nude mice. Thus, the tumor-suppressing effect of MZ could have been due to inhibition of tumor-induced angiogenesis.

In vivo angiogenesis was further assayed by the dorsal air-sac method (Tanaka et al., 1989). Subcutaneous neovascularization overlying a semipermeable membrane chamber containing A459 cells. The number and caliber of blood vessels were significantly reduced in mice fed orally with MZ as compared with control animals. In order to exclude the possibility that the reduced vasculature was due to lack of viable tumor cells in the chamber, cells were prelabeled with fluorescent dye and injected into the chamber. After the blood vessels were photographed, the tumor cells on the membrane was examined under a fluorescence microscope. Results indicated that both control and MZ-treated mice had similar cell densities on the membrane filters. Cells on the membranes from treated and control animals were further stained with Hoechst 33258, which revealed a number of apoptotic cells on the filter of MZ-treated mice, suggesting tumor cells on the membrane of MZ-treated cells had undergone apoptosis in vivo.

Figure 6:
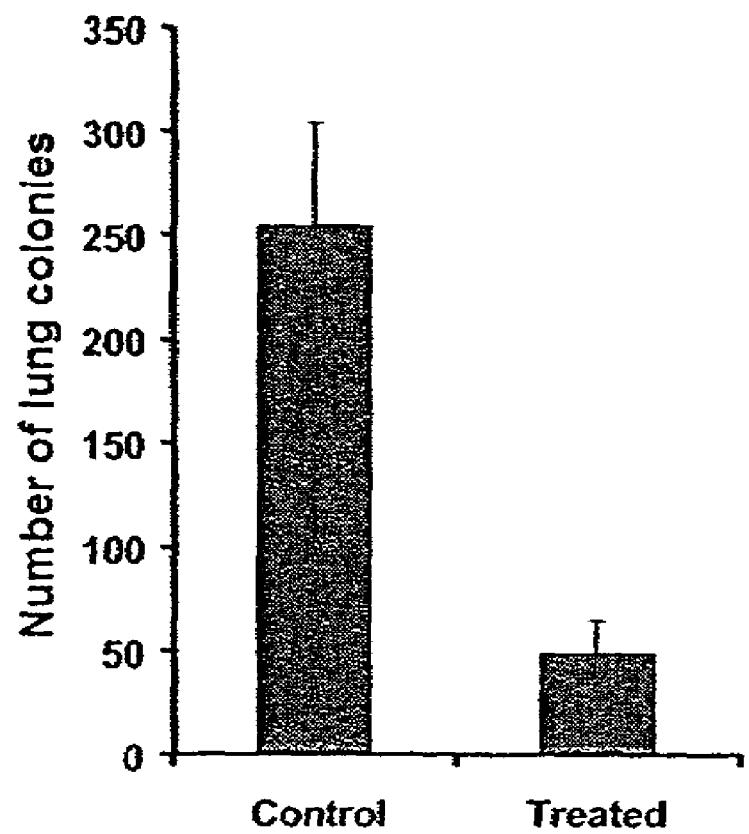
FIG. 6 Metastatic tumor colonies on lung surfaces. Number of lung surface colonies in control (C) and mebendazole (T) treated animals.

Next, the inventors asked whether treatment with MZ would inhibit the growth of human metastatic lung cancer cells in vivo. About 300 metastatic colonies appeared on untreated mice 21 days after A549 cell injection into the tail vein (FIG. 6). This technique was reproducible as the totals blindly counted by two investigators differed by less than 10%. This experiment was performed three times with similar results. The oral administration of 1 mg/ml MZ reduced mean colony count to 80% of the mean value for controls (P<0.0001). In other experiments groups treated with paclitaxel alone showed no significant reduction of colony formation. Histochemical staining of lung tissues with hematoxylin and eosin (H and E) indicated that not only the number of colonies but also the size of tumor colonies (as measured by the transverse diameter of the colony was significantly reduced by treatment with MZ.

MZ falls on the class of truly broad-spectrum antihelmintics with a high therapeutic index. Central to the success of this BZ group of antihelmintic drugs is their selective toxicity for helminths. Although the diverse activities of these compounds have been described at the biochemical and cellular levels, the molecular mechanism of this drug's action has not been explored in detail. The molecular mechanism by which the BZ group of drugs works in controlling the parasitic infection is controversial. The available evidence suggests that the mode of action involves their binding to and disrupting the functions of the microtubule system (Lacey et al., 1988; Lubega & Prichard, 1990; 1991; Lacey & Prichard, 1986). In vitro binding studies using enriched extracts from helminth and mammalian tubulin suggests tubulin as substrate for this drug (Lacey et al., 1988; Lubega & Prichard, 1990; Lacey & Prichard, 1986). It has been proposed that BZ compete for colchicine binding sites on the tubulin as a mechanism for their cytotoxicity in helminths (Lacey & Watson, 1985; 1999; Friedman & Platzer, 1978). BZ display selective toxicity toward nematodes when administered as antihelmintics and are not toxic to the host, unlike colchicine or other microtubule drugs.[12] Such selective toxicity is in contrast to the effect of BZ on the in vitro polymerization of mammalian tubulin and the growth of tumor cells (Davidse, 1986; Stearns et al., 1993; Nare et al., 1994) although differences in both the affinity between host and parasite macromolecules for BZ (Russell et al., 1992; Kohler & Bachmann, 1981) and the pharmacokinetics of BZ within the host and the parasite have been suggested as responsible for BZ selective toxicity (Gottschall et al., 1990). The nature of BZ selective toxicity remains elusive.

The observed safety of BZ as anthelmintics may also be unrelated to BZ-tubulin binding but instead be due to differences in metabolism or detoxification pathways, as suggested by (Nare et al., 1996) For example, the rapid and extensive metabolism of BZ into less toxic metabolite (e.g., sulfoxides and sulfones) by the liver microsomal enzymes (Lanusse et al., 1992a; 1992b; 1993) may account for some lack of host toxicity. Parasites, on the other hand, lack these metabolic pathways and are killed by BZ.

It has been shown recently that BZ are substrates for the P-glycoprotein transporter in multidrug-resistant tumor cells (Nare et al. 1994). It may be speculated that P-glycoprotein, which is overexpressed in several normal tissues and organs, could mediate the transport of BZ. Some terbenzimidazole compounds have been reported to be topoisomerase I poisons (Pilch et al., 1996). The inventors tested MZ for such an effect but could not detect any.

Figure 7:
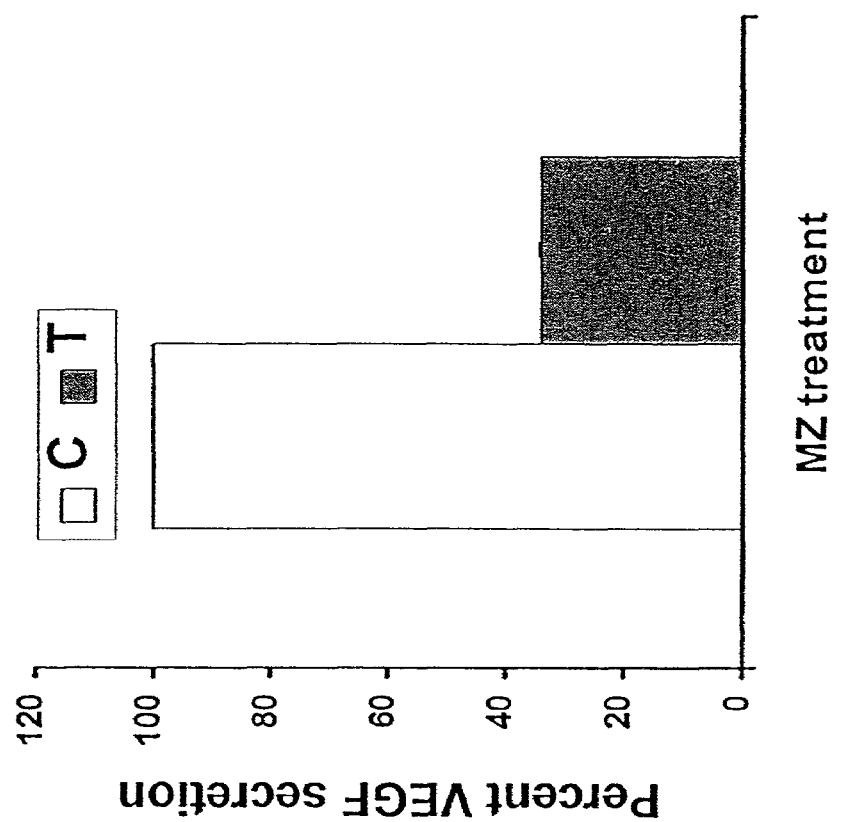
FIG. 7. Percent Inhibition of VEGF Expression in H460 Cell Line After MZ Treatment. Treatment period was 18 hours; control (C); treatment (T).

One of the most encouraging findings is that MZ inhibited the neovascularization in the human xenografts tested. In FIG. 7, a marked down-regulation of VEGF secretion following treatment with MZ was observed. Other data show that HUVEC cell tube formation in conditioned medium is inhibited following MZ treatment. The inventors have thus shown that MZ is a potent antiangiogeneic agent. It had no effect on endothelial cell growth, instead directly targeting tumor cells in vivo. MZ may be effective in the treatment of cancer and other angiogenesis-dependent diseases.

TABLE 5

Growth inhibitory effect of mebendazole on human tumor cell lines

| Cell Line | Tumor origin | Growth inhibition (%) |
|---|---|---|
| MCF-7 | Breast | 24.26 ± 8.4 |
| H460 | Lung | 25.23 ± 7.6 |
| H549 | Lung | 39.19 ± 10.7 |
| H322 | Lung | 68.50 ± 3.7 |
| H226Br | Lung | 64.24 ± 0.2 |
| H358 | Lung | 73.45 ± 1.8 |
| Saos-2 | Osteosarcoma | 65.36 ± 10.1 |
| SW480 | Colon | 63.63 ± 13.3 |
| MDA 231 | Breast | 66.24 ± 15.8 |
| SK-OV-433 | Ovarian | 28.15 ± 6.1 |
| RD | Rhabdomyosarcoma | 72.24 ± 2.8 |
| HT1080 | Osteosarcoma | 44.49 ± 7.7 |

The viability of the cells was measured after 24 h mebendazole treatment by trypan blue exclusion assay. The 100% value was derived from measurements obtained from untreated cells. Experiments were done in triplicate. Concentration of mebendazole = 0.05 ug/ml.

Example 5

MZ Increases Transgene Expression

Figure 8:
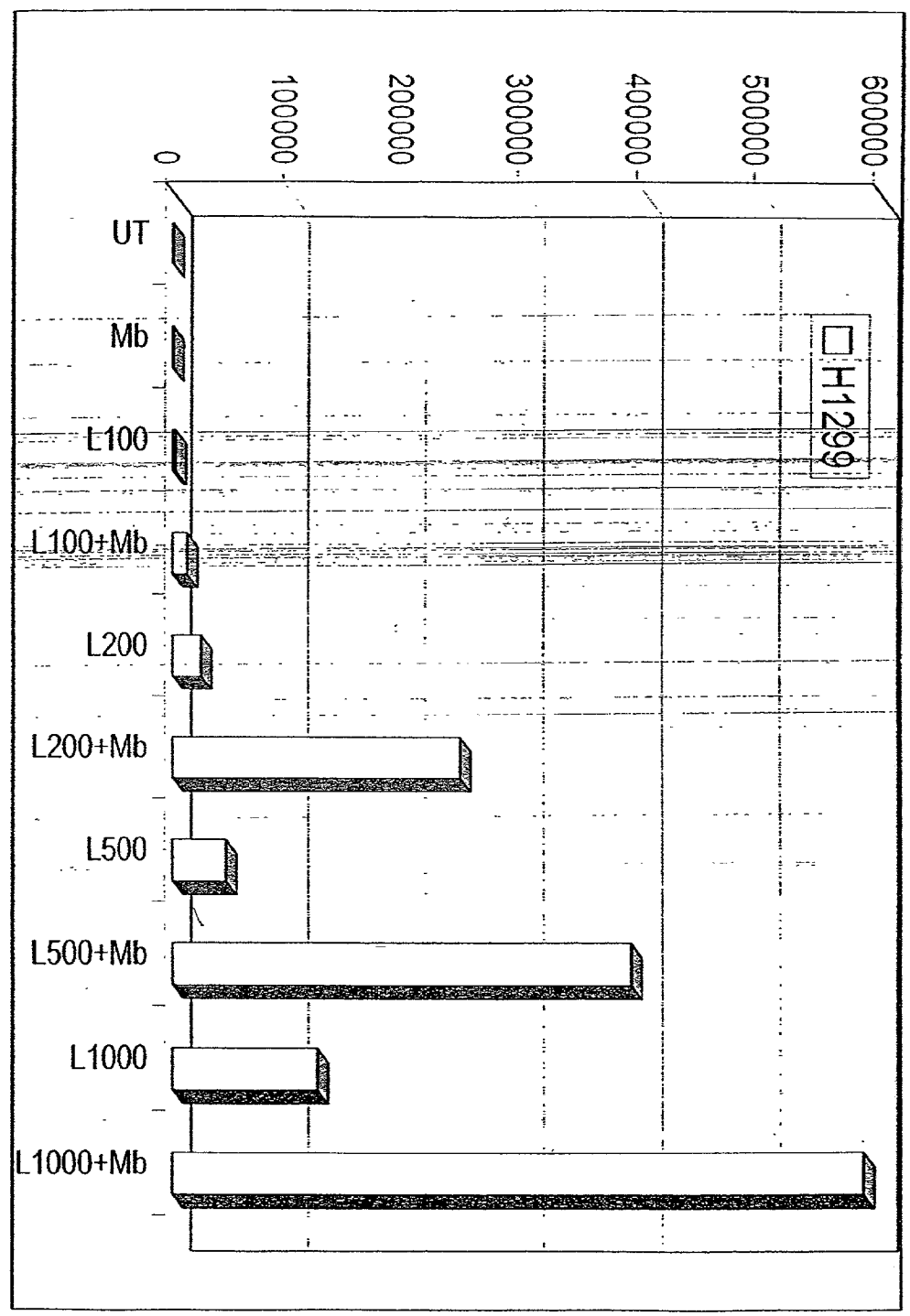
FIG. 8. Expression of Ad-luciferase in H1299 cells with and without MZ. H1299 cells were treated with media (UT) or Ad-luciferase at increasing multiplicities of infection, with or without MZ at 50 ng/ml. Forty-eight hours later, cells were harvested and luciferase activity assayed.
Figure 9:
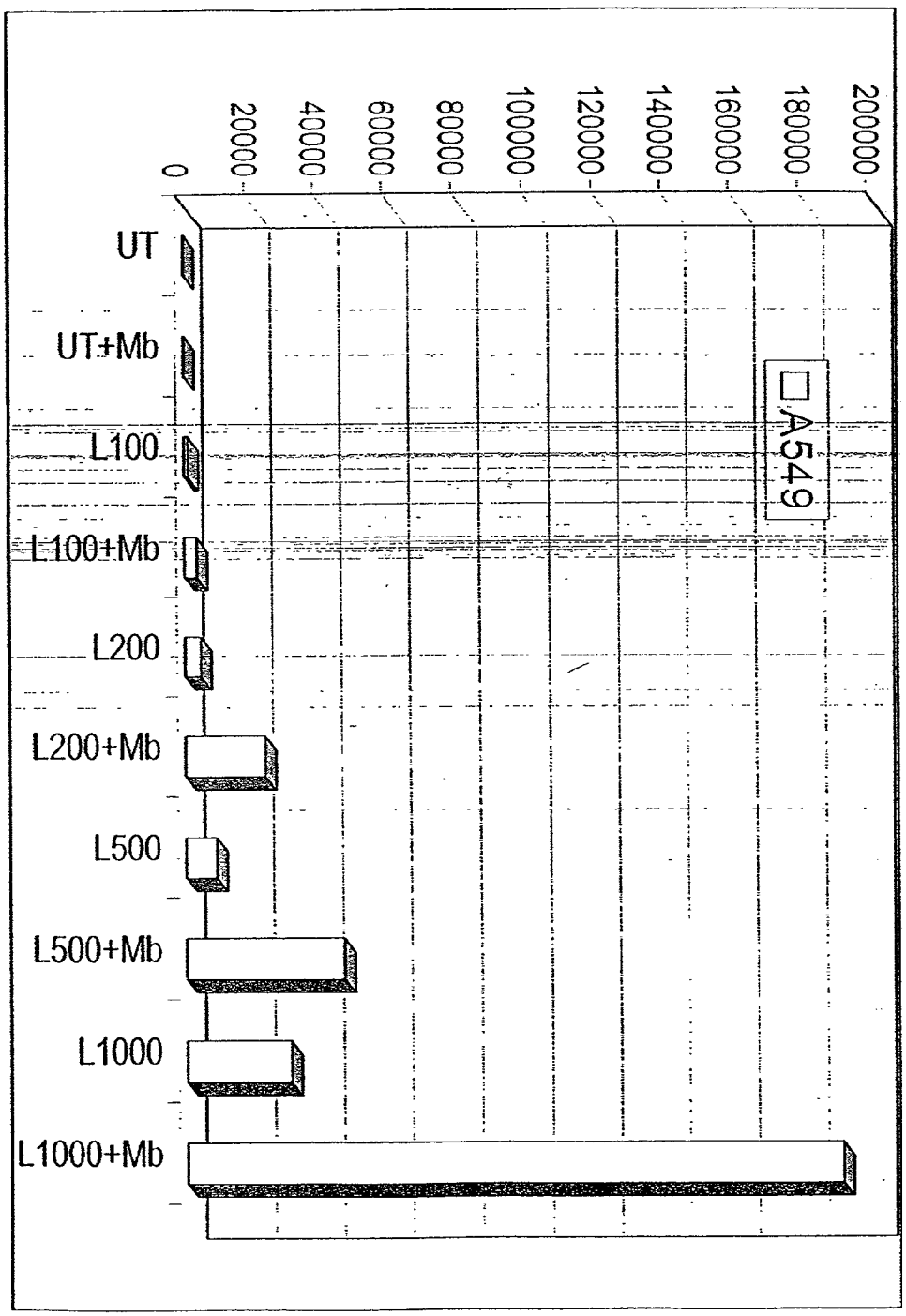
FIG. 9. Expression of Ad-luciferase in A549 cells with and without MZ. A549 cells were plated in 6-well dishes and either treated with media (UT) or Ad-luciferase at increasing multiplicities of infection, with or without MZ at 50 ng/ml. Forty-eight hours later, cells were harvested and luciferase activity assayed.

The inventors next attempted to determine if the effects MZ exhibited on p53 expression could be generalized. A first experiment revealed that MZ increased levels of adenovirus expressed MDA-7. Next, a series of six cell lines were transfected with Ad-luciferase at increasing multiplicities of infection, with or without MZ at 50 ng/ml. All six cell lines showed significant increases in transgene expression when treated with MZ. Data from two of these cell lines are shown in FIGS. 8 and 9.

Example 6

MZ Enhances Activity of Anti-Mictotic Drugs in H1460 NSCLC Cells

Figure 10:
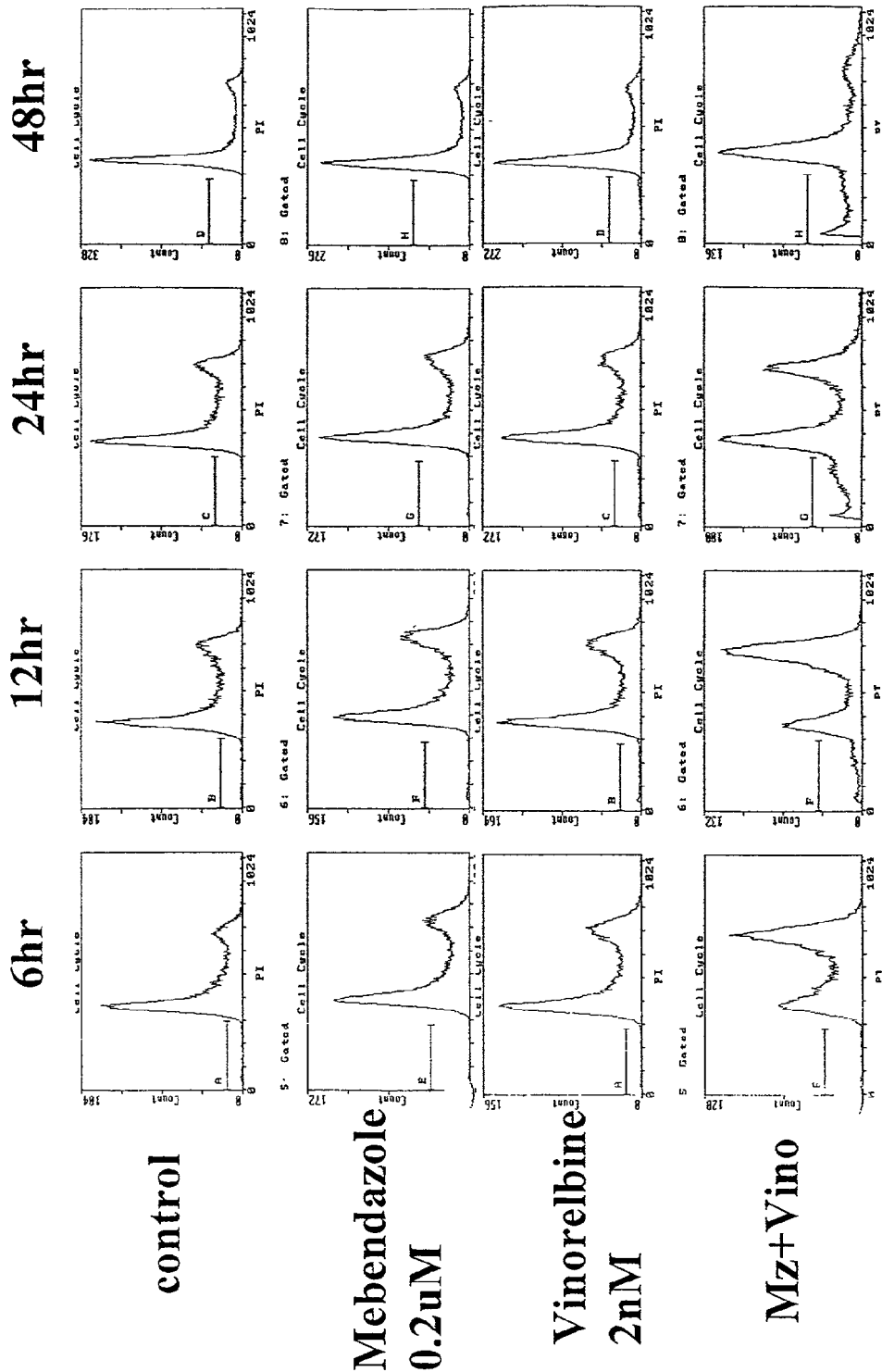
FIG. 10. MZ Enhances activity of anti-mictotic drugs in H460 NSCLC cells. H460 cells were treated with low dose of MZ or Vinorelbine. Cell cycle profiles indicating G1/S G2-Mphases were analyzed by FACS.

As shown in FIG. 10, H460 NSCLC cells were treated with low doses of MZ or Vinorelbine. When these two drugs were combined, a synergistic interaction between the two drugs was observed. This FACS-based assay shows cell cycle profiles indicating G1/S/G2-M cell cycle phases. The doses of MZ and vinorelbine were chosen to be "sub-therapeutic". The combination of drugs demonstrates enhanced G2-M block at 6-24 hr with pronounced apoptosis indicated by sub-G0 cells in the 24-48 hr cultures. No apoptosis was observed in control cultures or those treated with MZ or vinorelbine monotherapy. Thus, in H460 NSCLC cells mebendazole enhances the activity of anti-mitotic drugs.

Example 7

Microtuble Drug Resistant H460 Non-Small Cell Lung Cancer Cells (NSCLC)

The inventors have developed H460 NSCLC cell lines that are resistant to the microtubule drugs: taxol (7 nM) or vinorelbine (9 nM). These cell lines show a marked cross resistance to each other. For example Taxol resistant cells show resistance to Vinorelbine mediated cell death. Interestingly, when these drug resistant cells were exposed to MZ (0.5 µM) a significant cell death was observed (40-70%) at the 48 h time point. Thus, MZ can be effectively used for killing multi-drug resistant (MDR) cells in a clinical setting.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EP 0 273 085
U.S. Pat. No. 4,367,110
U.S. Pat. No. 4,452,901
U.S. Pat. No. 5,221,605
U.S. Pat. No. 5,238,808
U.S. Pat. No. 5,252,479
U.S. Pat. No. 5,310,687
U.S. Pat. No. 5,399,346
U.S. Pat. No. 5,672,344
U.S. Pat. No. 5,994,136
U.S. Pat. No. 6,013,516
U.S. Pat. No. 6,046,173
WO 98/32440
WO 98/51304
Abbondanzo et al., *Breast Cancer Res. Treat.*, 16:182 (#151) 1990.
Allred et al., *Breast Cancer Res. Treat.*, 16:182 (#149) 1990.
Almendro et al., *J Immunol* 1996 157(12):5411-21.
Angel et al., *Cell*, 49:729, 1987b.
Angel et al., *Mol. Cell. Biol.*, 7:2256, 1987a.
Arap et al., *Cancer Res.*, 55:1351-1354, 1995.
Atchison and Perry, *Cell*, 46:253, 1986.
Atchison and Perry, *Cell*, 48:121, 1987.
Banerji et al., *Cell*, 27:299, 1981.
Banerji et al., *Cell*, 35:729, 1983.
Barr et al., *Virology*, 96:656-659, 1979.
Bartek et al., *Oncogene*, 5:893-899, 1990.
Batterson and Roizman, *J. Virol.*, 46:371-377, 1983.
Bellamy et al., *Semin. Cancer Biol.*, 6:3-16, 1995.
Bellon et al., *de Ses Filiales*, 1996.
Benvenisty and Neshif, *Proc. Nat. Acad. Sci. USA*, 83:9551-9555, 1986.
Benvenisty and Neshif, *Proc. Nat'l Acad. Sci. USA*, 83:9551-9555, 1986.
Berkhout et al., *Cell*, 59:273, 1989.
Berns and Bohensky, *Adv. Virus Res.*, 32:243-307, 1987.
Berns and Giraud, *Curr. Top. Microbiol. Immunol.*, 218:1-23, 1996.
Berns, *Microbiol Rev*, 54(3):316-29, 1990.
Bertran et al., *J Virol*, 70(10):6759-66, 1996.
Blanar et al., *EMBO J.*, 8:1139, 1989.
Bodine and Ley, *EMBO J.*, 6:2997, 1987.

Boshart et al., *Cell*, 41:521, 1985.
Bossche et al., *Chemotherapy of Gastrointestinal Helminths.*, 1985.
Bosze et al., *EMBO J.*, 5:1615, 1986.
Braddock et al., *Cell*, 58:269, 1989.
Bressac et al., *Proc. Natl. Acad. Sci. U.S.A.*, 87:1973-1977, 1990.
Brown et al., *Breast Cancer Res. Treat.*, 16:192(#191), 1990.
Bulla and Siddiqui, *J. Virol.*, 62:1437, 1986.
Bussemakers et al., *Cancer Res.*, 52:2916-2922, 1992.
Caldas et al., *Nature Genetics*, 8:27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Canman et al., *Genes Dev.*, 9:600-611, 1995.
Casey et al., *Oncogene* 6:1791-1797, 1991.
Celander and Haseltine, *J. Virology*, 61:269, 1987.
Celander et al., *J. Virology*, 62:1314, 1988.
Chander et al., *Br. J. Cancer*, 65:208-214, 1992.
Chandler et al., *Cell*, 33:489, 1983.
Chang et al., *Mol. Cell. Biol.*, 9:2153, 1989.
Chatterjee et al., *Proc. Nat'l Acad. Sci. USA.*, 86:9114, 1989.
Chen and Okayama, *Mol. Cell. Biol.*, 7:2745-2752, 1987.
Cheng et al., *Cancer Res.*, 54:5547-5551, 1994.
Cheung et al., *J Biol Chem*, 268(32):24303-24310, 1993.
Choi et al., *Cell*, 53:519, 1988.
Coffin, *In: Fields, Virology*, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Cripe et al., *EMBO J.*, 6:3745, 1987.
Culotta and Hamer, *Mol. Cell. Biol.*, 9:1376, 1989.
Dandolo et al., *J. Virology*, 47:55, 1983.
Davidse, *Ann. Rev. Phytopathol.*, 24:43-65, 1986.
De Villiers et al., *Nature*, 312:242; 1984.
DeLuca et al., *J. Virol.*, 56:558-570, 1985.
Deschamps et al., *Science*, 230:1174, 1985.
Dubensky et al., *Proc. Nat'l Acad. Sci. USA*, 81:7529-7533, 1984.
Edbrooke et al., *Mol. Cell. Biol.*, 9:1908, 1989.
Edelman and Crossini, *Ann. Rev. Biochem.*, 60:155-190, 1991.
Edelman, *Ann. Rev. Biochem.*, 54:135-169, 1985.
Edlund et al., *Science*, 230:912, 1985.
Elroy-Stein et al., *Proc. Nat'l Acad. Sci. USA*, 1989.
Elshami et al., *Gene Therapy*, 7:141-148, 1996.
Fearon et al., *Science*, 247:49-56, 1990.
Fechheimer et al., *Proc. Nat'l. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Foecking and Hofstetter, *Gene*, 45:101, 1986.
Folkman, *Nat Med*, 1:27-31, 1995b.
Folkman, *Mol Med*, 1(2):120-122, 1995a.
Folkman J. Anti-angiogenesis: new concept for therapy of solid tumors. Ann Surg 1972 March; 175(3):409-16.
Fraley et al., *Proc. Nat'l Acad. Sci. USA*, 76:3348-3352, 1979.
Freedman and Levine, *Mol. Cell. Biol.*, 18:7288-7293, 1998.
French et al., *Circulation*, 90: 2414-2424, 1994.
Friedman and Platzer, *Biochim. Biophys. Acta*, 544:605-614, 1978.
Friedman and Platzer, *Biochim. Biophys. Acta*, 630:271-278, 1980.
Fritsche et al., *Oncogene* 8:307-318, 1993.
Frixen et al., *J. Cell Biol.*, 113:173-185, 1991.
Fujita et al., *Cell*, 49:357, 1987.
Ghosh and Bachhawat, In: Wu, G, Wu C, eds. Liver diseases, targeted diagnosis and therapy using specific receptors and ligands. New York: Marcel Dekker, pp. 87-104, 1991.
Ghosh-Choudhury et al., *EMBO J.*, 6:1733-1739, 1987.
Giancotti and Ruoslahti, *Cell*, 60:849-859, 1990.
Gilles et al., *Cell*, 33:717, 1983.
Ginsburg et al., *Proc. Nat'l Acad. Sci. USA*, 88:1651-1655, 1991.
Glorioso et al., *Ann. Rev. Microbiol.*, 49:675-710, 1995.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Gonzalez-Zulueta, *Cancer Res* 55(20):4531-4535, 1995.
Goodbourn and Maniatis, *Proc. Nat'l Acad. Sci. USA*, 85:1447, 1988.
Goodbourn et al., *Cell*, 45:601, 1986.
Gopal, *Mol. Cell. Biol.*, 5:1188-1190, 1985.
Gottlieb and Oren, *Biochim. Biophys. Acta*, 1287:77-102, 1996.
Gottschall et al., *Parasitol. Today*, 6:115 1990.
Graham and Prevec, In: Methods in Molecular Biology: Gene Transfer and Expression Protocols 7, E. J. Murray (ed.), Clifton, N.J., Humana Press, pp. 205-225, 1991.
Graham and Van Der Erb, *Virol.*, 52:456-467, 1973.
Graham et al., *J. Gen. Virol.*, 36:59-72, 1977.
Greene et al., *Immunology Today*, 10:272, 1989.
Griffiths et al., *Oncogene*, 14:523-531, 1997.
Grosschedl and Baltimore, *Cell*, 41:885, 1985.
Grunhaus and Horwitz, *Sem. Virol.*, 3:237-252, 1992.
Hainaut, *Curr. Opin. Oncol.*, 7:76-82, 1995.
Hamada et al., *Gynecol. Oncol.*, 63:219-227, 1996.
Harlan and Weintraub, *J. Cell Biol.*, 101: 1094-1099, 1985.
Haslinger and Karin, *Proc. Nat'l Acad. Sci. USA.*, 82:8572, 1985.
Hauber and Cullen, *J. Virology*, 62:673, 1988.
Haupt et al., *Genes Dev.*, 9:2170-2183, 1995.
Haynes et al., *J. Virol.*, 67, 2486-2495, 1993.
Hen et al., *Nature*, 321:249, 1986.
Hensel et al., *Lymphokine Res.*, 8:347, 1989.
Herman et al., *Cancer Res.*, 55:4525-4530, 1995.
Herr and Clarke, *Cell*, 45:461, 1986.
Hersdorffer et al., *DNA Cell Biol.*, 9: 713-723, 1990.
Herz and Gerard, *Proc. Nat'l Acad. Sci. USA*, 90: 2812-2816, 1993.
Hinds et al., *Cell Growth Differ.*, 1:571-580, 1990.
Hirochika et al., *J. Virol.*, 61:2599, 1987.
Hirsch et al., *Mol. Cell. Biol.*, 10:1959, 1990.
Holbrook et al., *Virology*, 157:211, 1987.
Holland et al., *Virology*, 101:10-18, 1980.
Hollstein et al., *Science*, 253:49-53, 1991.
Honess and Roizman, *J. Virol.*, 14:8-19, 1974.
Honess and Roizman, *J. Virol.*, 16: 1308-1326, 1975.
Horlick and Benfield, *Mol. Cell. Biol.*, 9:2396, 1989.
Huang et al., *Cell*, 27:245, 1981.
Hug et al., *Mol Cell Biol*, 8(8):3065-3079, 1988.
Hussussian et al., *Nature Genetics*, 8:15-21, 1994.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jiang et al., *Proc. Nat'l Acad. Sci. USA*, 93:9160-9165, 1996.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.

Kamb et al., *Nature Genetics*, 8:22-26, 1994.
Kaneda et al., *Science*, 243:375-378, 1989.
Karin et al., *Mol. Cell. Biol.*, 7:606, 1987.
Katinka et al., *Cell*, 20:393, 1980.
Katinka et al., *Nature*, 290:720, 1981.
Kato et al., *J. Biol. Chem.*, 266:3361-3364, 1991.
Kawamoto et al., *Mol. Cell. Biol.*, 8:267, 1988.
Kerns et al., *Gene Therapy*, 3:748-755, 1996.
Kiledjian et al., *Mol. Cell. Biol.*, 8:145, 1988.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kohler and Bachmann, *Mol. Biochem. Parasitol.*, 4:325-336, 1981.
Korin et al., *Genomics*, 10:831-834, 1991.
Kotin and Berns, *Virol.*, 170:460-467, 1989.
Kotin et al., *Proc. Nat'l Acad. Sci. USA*, 87:2211-2215, 1990.
Kotin et al., *Genomics*, 10(3):831-4, 1991.
Kraiss et al., *Exp. Cell Res.*, 192:157-164, 1991.
Kraus et al., *FEBS Lett*, 428(3): 165-170, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., In: *Gene Expression*, D. Hamer and M. Rosenberg, eds., New York: Alan R. Liss, 1983.
Kuhl et al., *Cell*, 50:1057, 1987.
Kunz et al., *Nucl. Acids Res.*, 17:1121, 1989.
Lacey and Watson, *Biochem. Pharmacol.*, 34:1073-1077, 1989.
Lacey and Watson, *Biochem. Pharmacol.*, 34:1073-1077, 1999.
Lacey and Watson, *Biochem. Pharmacol.*, 34:3603-3605, 1985.
Lacey and Prichard, Mol Biochem Parasitol, 19(2):171-181, 1986.
Lacey, *Int. J. Parasitol.*, 18:885-936, 1988.
Lanusse et al., *J Vet Pharmacol Ther*, 15(3):267-74, 1992a.
Lanusse et al., *Xenobiotica*, 23(3):285-95, 1993.
Lareyre et al., *J Biol Chem*, 274(12):8282-8290, 1992.
Larsen et al., *Proc. Nat'l Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Mol. Endocrinol.*, 2: 404-411, 1988.
Lee et al., *Nature*, 294:228, 1981.
Lee et al., *DNA Cell Biol*, 16(11):1267-1275, 1997.
Levero et al., *Gene*, 101: 195-202, 1991.
Levinson et al., *Nature*, 295:79, 1982.
Lin and Guidotti, *J. Biol. Chem.*, 264:14408-14414, 1989.
Lin et al., *Mol. Cell. Biol.*, 10:850, 1990.
Liu et al. *Nature* 384:273-276, 1996.
Lowe et al., *Curr. Opin. Oncol.*, 7:547-553, 1995.
Lubiga, and Prichard, *Mol. Biochem. Parasitol.*, 38:221-232, 1990.
Luria et al., *EMBO J.*, 6:3307, 1987.
Lusky and Botchan, *Proc. Nat'l Acad. Sci. USA*, 83:3609, 1986.
Lusky et al., *Mol. Cell. Biol.*, 3:1108, 1983.
Majors and Varmus, *Proc. Nat'l Acad. Sci. USA.*, 80:5866, 1983.
Mann et al., *Cell*, 33:153-159, 1983.
Markowitz et al., *J. Virol.*, 62:1120-1124, 1998.
Matsura et al., *Br. J. Cancer*, 66:1122-1130, 1992.
McNeall et al., *Gene*, 76:81, 1989.
Merlo et al., *Nat Med*, 1(7):686-92, 1995.
Miksicek et al., *Cell*, 46:203, 1986.
Mitsudomi et al., *Oncogene*, 7:171-180, 1992.
Miyashita and Reed, *Cell*, 80:293-299, 1995.
Mizukami et al., *Virology*, 217:124-130, 1996.
Monthenarh *Critical Review and Oncogenesis* 3:233-256, 1992.
Montross et al., *J. Virol*, 65:4991-4998, 1991.
Mordacq and Linzer, *Genes and Dev.*, 3:760, 1989.
Moreau et al., *Nucl. Acids Res.*, 9:6047, 1981.
Mori et al., *Cancer Res.*, 54:3396-3397, 1994.
Muesing et al., *Cell*, 48:691, 1987.
Mulligan et al., *J Immunol*, 151(11):6410-6417, 1993.
Naldini, et al., In vivo gene delivery and stable transduction of nondividing cells by a lentiviral vector, 1996.
Naldini, et al., *Science*, 272(5259):263-267, 1996.
Nare, et al., *J Biol Chem*, 12; 271(15):8575-8581, 1996.
Nare et al., *Biochem. Pharmacol.*, 48:2215-2222, 1994.
Negrini et al., *Cancer Res.*, 54:1818-1824, 1994.
Ng et al., *Nuc. Acids Res.*, 17:601, 1989.
Nicolas and Rubenstein, et al., *Vectors*, 493-513, 1988.
Nicolau and Sene, *Biochim. Biophys. Acta*, 721:185-190, 1982.
Nicolau et al., *Methods Enzymol.*, 149:157-176, 1987.
Nigro et al., *Nature*, 342:705-708, 1989.
Nobori et al., *Nature*, 368:753-756, 1995.
Nomoto et al., *Gene*, 236(2):259-271, 1999.
Obrink, *BioEssays*, 13:227-233, 1991.
Odin and Obrink, *Exp. Cell Res.*, 171:1-15, 1987.
Ogawa, *Neuropathologica*, 77:244-253, 1989.
Okamoto et al., *Proc. Nat'l Acad. Sci. USA*, 91:11045-11049, 1994.
Ondek et al., *EMBO J.*, 6:1017, 1987.
Orlow et al., *Cancer Res.*, 54:2848-2851, 1994.
Ornitz et al., *Mol. Cell. Biol.*, 7:3466, 1987.
Ostrove et al., *Virology*, 113:532-533, 1981.
Palmiter et al., *Nature*, 300:611, 1982.
Paskind et al., *Virology*, 67:242-248, 1975.
Pech et al., *Mol. Cell. Biol.*, 9:396, 1989.
Perales et al., *Proc. Nat'l. Acad. Sci. USA*, 81:7161-7165, 1994.
Perdomo et al., *Cancer Res Clin Oncol.*, 124:10-18, 1998.
Perez-Stable and Constantini, *Mol. Cell. Biol.*, 10:1116, 1990.
Picard and Schaffner, *Nature*, 307:83, 1984.
Pilch et al. *Drug Des Discov*, 13(3-4):115-33, 1996.
Pinkert et al., *Genes and Dev.*, 1:268, 1987.
Ponnazhagen et al., *Human Gene Therapy*, 8:275-284, 1997.
Ponnazhagen et al., *J. Gen. Virol.*, 77:1111-1122, 1996.
Ponta et al., *Proc. Nat'l Acad. Sci. USA.*, 82:1020, 1985.
Porton et al., *Mol. Cell. Biol.*, 10:1076, 1990.
Post et al., *Cell*, 24:555-565, 1981.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Radler et al., *Science*, 275: 810-814, 1997.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., pp. 642-652, 1035-1038 and 1570-1580.
Remington's Pharmaceutical Sciences, 18th ed., pp. 1534.
Resendez Jr. et al., *Mol. Cell. Biol.*, 8:4579, 1988.
Rich et al., *Human Gene Therapy*, 4:461-476, 1993.

Ripe et al., *Mol. Cell. Biol.*, 9:2224, 1989.
Rippe et al., *Mol. Cell. Biol.*, 10:689-695, 1990.
Rittling et al., *Nucl. Acids Res.*, 17:1619, 1989.
Roizman and Sears, In *Field's Virology*, 3rd edition, ed. Fields et al., 2231-2295, 1995.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Nat'l Acad. Sci. USA*, 86:9079-9083, 1989.
Russell et al., *Biochem. Pharmacol.*, 43:1095-1100, 1992.
Sambrook, Fritsch, Maniatis, In: *Molecular Cloning: A Laboratory Manual* 2 rev. ed., Cold Spring Harbor, Cold Spring Harbor Laboratory Press, 1(77): 19-17.29, 1989.
Samulski et al., *EMBO J.*, 10:3941-3950, 1991.
Sandig et al., 12th Meeting of the European Society for Animal Cell Technology, May, 1993.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Serrano et al., *Nature*, 366:704-707, 1993.
Serrano et al., *Science*, 267:249-252, 1995.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Slilaty et al., *Science*, 220:725-727, 1983.
Smith and Moss, *Gene*, 25:21-28, 1983.
Song et al., *Human Gene Therapy*, 8: 1207-1217, 1997.
Spalholz et al., *Cell*, 42:183, 1985.
Spandau and Lee, *J. Virology*, 62:427, 1988.
Spandidos and Wilkie, *EMBO J.*, 2:1193, 1983.
Srivastava et al., *J. Virol.*, 45:555-564, 1983.
Stearns et al., *Cancer Res*, 53(13):3073-7, 1993.
Stephens and Hentschel, *Biochem. J.*, 248:1, 1987.
Stratford-Perricaudet and Perricaudet, In: Human Gene Transfer. 1991.
Stratford-Perricaudet, et al., *Human Gene Therapy*, 1: 241-256, 1991.
Stratton et al., *Oncogene*, 5:1297-1301, 1990.
Stuart et al., *Nature*, 317:828, 1985.
Su et al., *Proc. Nat'l Acad. Sci. USA*, 95:14400-14405, 1998.
Sullivan and Peterlin, *Mol. Cell. Biol.*, 7:3315, 1987.
Swartzendruber and Lehman, *J. Cell. Physiology*, 85:179, 1975.
Takahashi et al., *Science*, 246:491-494, 1989.
Takahasi et al., *Cancer Res.*, 52: 2340-2342, 1992.
Takebe et al., *Mol. Cell. Biol*, 8:466, 1988.
Tarunina and Jenkins, *Oncogene*, 8:3165-3173, 1993.
Tavernier et al., *Nature*, 301:634, 1983.
Taylor and Kingston, *Mol. Cell Biol*, 10:165, 1990a.
Taylor and Kingston, *Mol. Cell. Biol.*, 10:176, 1990b.
Taylor et al., *J. Biol. Chem.*, 264:15160, 1989.
Temin, In: Kucherlapti R, ed. Gene Transfer. New York: Plenum Press, pp. 149-188, 1986.
Thiesen et al., *J. Virology*, 62:614, 1988.
Top et al., *J. Infect. Dis.*, 124:155-160, 1971.
Treisman, *Cell*, 42:889, 1985.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsumaki et al., *J Biol Chem*, 273(36):22861-22864, 1998.
Tur-Kaspa et al., *Mol. Cell Biol.*, 6:716-718, 1986.
Tyndall et al., *Nuc. Acids. Res.*, 9:6231, 1981.
Umbas et al., *Cancer Res.*, 52:5104-5109, 1992.
Vannice and Levinson, *J. Virology*, 62:1305, 1988.
Varmus et al., *Cell*, 25:23-36, 1981.
Vasseur et al., *Proc. Nat'l Acad. Sci. USA.*, 77:1068, 1980.
Wagner et al., *Genes Dev.*, 8:2817-2830, 1994.
Wagner et al., *Proc. Nat'l Acad. Sci. USA*, 87:3410-3414, 1990.
Wang and Calame, *Cell*, 47:241, 1986.
Watt et al., *Proc. Nat'l Acad. Sci. USA*, 83:3166-3170, 1986.
Weber et al., *Cell*, 36:983, 1984.
Weinberg, *Science*, 254:1138-1145, 1991.
Weinberger et al. *Mol. Cell. Biol.*, 8:988, 1984.
Werthman et al., *J. Urolog.*, 155:753-756, 1996.
Winoto and Baltimore, *Cell*, 59:649, 1989.
Wolf et al., In: *Ovarian Cancer*, 259-271, 1998.
Wong et al., *Gene*, 10: 87-94, 1980.
Wu and Wu, *Adv. Drug Delivery Rev.*, 12:159-167, 1993.
Wu and Wu, *Biochem.*, 27:887-892, 1988.
Wu and Wu, *J. Biol. Chem.*, 262:4429-4432, 1987.
Wu H K, Squire J A, Song Q, Weksberg R. Promoter-dependent tissue-specific expressive nature of imprinting gene, insulin-like growth factor II, in human tissues. Biochem Biophys Res Commun 1997 Apr. 7; 233(1):221-6.
Yang et al., *Proc. Nat'l Acad. Sci. USA*, 87:9568-9572, 1990.
Yonish-Rouach, *Experientia*, 52:1001-1007, 1996.
Yutzey et al. *Mol. Cell. Biol.*, 9:1397, 1989.
Zhao-Emonet et al., *Biochim Biophys Acta*, 442(2-3): 109-19, 1998.
Zufferey et al., *Nat Biotechnol*, 15(9):871-5, 1997.

What is claimed is:

1. A method for inducing apoptosis in a tumor cell expressing a tumor suppressor gene, comprising the steps of:
   (1) determining the tumor suppressor gene status of the tumor cell; and
   (2) administering an effective amount of a benzimidazole to said tumor cell, wherein expression of the tumor suppressor gene by the tumor cell and benzimidazole results in the apoptosis of the tumor cell.

2. The method of claim 1, wherein the benzimidazole is a derivative having the formula:

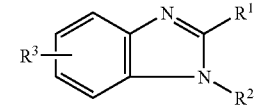

wherein $R^3$ is selected from the group consisting of H, carboxyl ($-CO_2H$), hydroxyl, amino, chloro, difluormethoxy, benzoyl, phenyl-thio, pyridinyl, propyl-thio, diphenyl, methoxy, fluorophenylmethyl-2-chloro, propenyl, chloropropyl or esters ($-CO_2R^4$) wherein $R^4$ is selected from the group consisting of alkoxy, haloalkyl, alkenyl, and cycloalkyl, wherein the alkyl groups have from 1-8 carbons, or $CH_3CH_2(OCH_2CH_2)_n-$, or $CH_3CH_2CH_2(OCH_2CH_2CH_2)_n-$, or $(CH_3)_2CH(OCH(CH_3)CH_2)_n-$, wherein n is from 1-3, wherein $R^1$ is OH, Cl, SH, (methoxy-dimethylpyridinyl)methyl-(sulfonyl), carbamate or piperidin-4-yl, and $R^2$ is hydrogen, α-methylvinyl, 3-chloropropyl or piperidin-4-yl, or the pharmaceutically effective organic or inorganic salts thereof, or mixtures thereof.

3. The method of claim 2, wherein the benzimidazole derivative is methyl 5-benzoylbenzimidazole-2-carbamate (mebendazole).

4. The method of claim 2, wherein the benzimidazole derivative is methyl 5-(phenylthio)-2-benzimidazole carbamate (fenbendazole).

5. The method of claim 2, wherein the benzimidazole derivative is 5-methoxy-2-[[(4-methoxy-3,5-dimethyl-2-pyridinyl)methyl]sulfinyl]-1H-benzimidazole (omeprazole).

6. The method of claim 2, wherein the benzimidazole derivative is

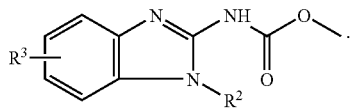

7. The method of claim 2, wherein the benzimidazole derivative is

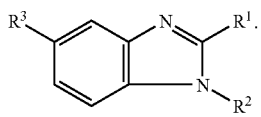

8. The method of claim 2, wherein the benzimidazole derivative is

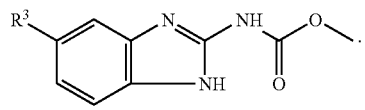

9. The method of claim 1, wherein benzimidazole administration is repeated at least once.

10. The method of claim 1, wherein said method is used to treat rheumatoid arthritis, inflammatory bowel disease or restenosis.

11. The method of claim 1, wherein the tumor cell is a multidrug resistant tumor cell.

12. The method of claim 11, wherein the multidrug resistant tumor cell is a lung tumor cell, a non-small cell lung carcinoma cell, a breast cancer cell, or a sarcoma cell.

13. The method of claim 1, wherein the tumor cell is a lung tumor cell.

14. The method of claim 13, wherein the lung tumor cell is a non-small cell lung carcinoma cell.

15. The method of claim 1, wherein the tumor cell is a breast cancer cell.

16. The method of claim 1, wherein the tumor cell is a sarcoma cell.

17. The method of claim 1, wherein the tumor suppressor gene is p53, p16, p21, Rb, p15, BRCA1, BRCA2, zac1, p73, ATM, HIC-1, DPC-4, FHIT, NF2, APC, DCC, PTEN, ING1, NOEY1, NOEY2, PML, OVCA1, MADR2, WT1, 53BP2, IRF-1, MDA-7 and C-CAM.

18. The method of claim 1, wherein the tumor suppressor gene is MDA-7.

19. The method of claim 1, wherein the tumor suppressor gene is p53.

20. The method of claim 1, wherein determining comprises Southern blotting.

21. The method of claim 1, wherein determining comprises Northern blotting.

22. The method of claim 1, wherein determining comprises PCR.

23. The method of claim 1, wherein determining comprises ELISA.

24. The method of claim 1, wherein determining comprises Western blotting.

25. The method of claim 1, wherein determining comprises immunofluorescence.

26. The method of claim 1, wherein the tumor cell expresses a functional tumor suppressor gene.

27. A method for treating a patient having cancer wherein cancer cells express a tumor suppressor, comprising the steps of:
  (1) determining the tumor suppressor gene status of the cancer cell; and
  (b) administering an effective amount of a benzimidazole to said patient, wherein the expression of the tumor suppressor gene by the cancer cell and the administration of the benzimidazole results in the inhibition of said cancer.

28. The method of claim 27, wherein the benzimidazole is a derivative having the formula:

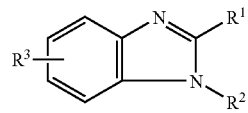

wherein $R^3$ is selected from the group consisting of H, carboxyl ($-CO_2H$), hydroxyl, amino, chloro, difluormethoxy, benzoyl, phenyl-thio, pyridinyl, propyl-thio, diphenyl, methoxy, fluorophenylmethyl-2-chloro, propenyl, chloropropyl or esters ($-CO_2R^4$) wherein $R^4$ is selected from the group consisting of alkoxy, haloalkyl, alkenyl, and cycloalkyl, wherein the alkyl groups have from 1-8 carbons, or $CH_3CH_2(OCH_2CH_2)_n-$, or $CH_3CH_2CH_2(OCH_2CH_2CH_2)_n-$, or $(CH_3)_2CH(OCH(CH_3)CH_2)_n-$, wherein n is from 1-3, wherein $R^1$ is OH, Cl, SH, (methoxy-dimethyl,pyridinyl)methyl-(sulfonyl), carbamate or piperidin-4-yl, and $R^2$ is hydrogen, a-methylvinyl, 3-chloropropyl or piperidin-4-yl, or the pharmaceutically effective organic or inorganic salts thereof, or mixtures thereof.

29. The method of claim 27, wherein the benzimidazole derivative is methyl 5-benzoylbenzimidazole-2-carbamate (mebendazole).

30. The method of claim 27, wherein the benzimidazole derivative is methyl 5-(phenylthio)-2-benzimidazole carbamate (fenbendazole).

31. The method of claim 27, wherein the benzimidazole derivative is 5 methoxy-2-[[(4-methoxy-3,5-dimethyl-2-pyridinyl)methyl]sulfinyl]-1H-benzimidazole (omeprazole).

32. The method of claim 27, wherein the benzimidazole derivative is

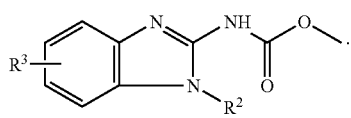

33. The method of claim 27, wherein the benzimidazole derivative is

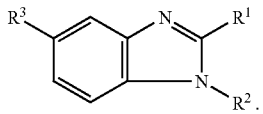

34. The method of claim 27, wherein the benzimidazole derivative is

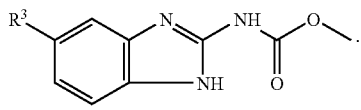

35. The method of claim 27, wherein the tumor suppressor gene is p53, p16, p21, Rb, p15, BRCA1, BRCA2, zac1, p73, ATM, HIC-1, DPC-4, FHIT, NF2, APC, DCC, PTEN, ING1, NOEY1, NOEY2, PML, OVCA1, MADR2, WT1, 53BP2, IRF-1, MDA-7 and C-CAM.

36. The method of claim 27, wherein the tumor suppressor gene is MDA-7.

37. The method of claim 27, wherein the tumor suppressor gene is p53.

38. The method of claim 27, wherein the cancer cell is a multidrug resistant tumor cell.

39. The method of claim 38, wherein the multidrug resistant tumor cell is a lung tumor cell, a non-small cell lung carcinoma cell, a breast cancer cell, or a sarcoma cell.

40. The method of claim 27, wherein the cancer cell is a lung tumor cell.

41. The method of claim 40, wherein the lung tumor cell is a non-small cell lung carcinoma cell.

42. The method of claim 27, wherein the cancer cell is a breast cancer cell.

43. The method of claim 27, wherein the cancer cell is a sarcoma cell.

44. The method of claim 27, wherein benzimidazole administration comprises intratumoral administration.

45. The method of claim 27, wherein benzimidazole administration comprises systemic administration.

46. The method of claim 27, wherein benzimidazole administration comprises oral administration.

47. The method of claim 27, wherein benzimidazole administration comprises administration in the area local to a tumor in said patient.

48. The method of claim 27, wherein benzimidazole administration comprises administration in the area regional to a tumor in said patient.

49. The method of claim 27, wherein benzimidazole administration is repeated at least once.

50. The method of claim 27, wherein the dose of benzimidazole is about 0.1 mg per kg body weight.

51. The method of claim 27, wherein the dose of benzimidazole is about 1.0 mg per kg body weight.

52. The method of claim 27, wherein determining comprises Southern blotting.

53. The method of claim 27, wherein determining comprises Northern blotting.

54. The method of claim 27, wherein determining comprises PCR.

55. The method of claim 27, wherein determining comprises ELISA.

56. The method of claim 27, wherein determining comprises Western blotting.

57. The method of claim 27, wherein determining comprises immunofluorescence.

* * * * *

UNITED STATES PATENT AND TRADEMARK OFFICE
CERTIFICATE OF CORRECTION

PATENT NO.        : 7,423,015 B1
APPLICATION NO. : 10/043877
DATED             : September 9, 2008
INVENTOR(S)       : Tapas Mukhopadhyay It is certified that error appears in the above-identified patent and that said Letters Patent is hereby corrected as shown below:

In claim 2, column 52, lines 48-49, delete "difluormethoxy" and insert --difluoromethoxy-- therefor.

In claim 28, column 54, line 34, delete "difluormethoxy" and insert --difluoromethoxy-- therefor.

In claim 28, column 54, line 44, delete "a-methylvinyl" and insert --α-methylvinyl-- therefor.

Signed and Sealed this

Tenth Day of February, 2009

JOHN DOLL
*Acting Director of the United States Patent and Trademark Office*